(12) United States Patent
Tsuta

(10) Patent No.: US 8,162,481 B2
(45) Date of Patent: Apr. 24, 2012

(54) METHOD FOR STATIC VISUAL FIELD SCANNING APPARATUS

(75) Inventor: Tomohiro Tsuta, Kobe (JP)

(73) Assignee: Tomohiro Tsuta, Kobe (JP)

( * ) Notice: Subject to any disclaimer, the term of this patent is extended or adjusted under 35 U.S.C. 154(b) by 0 days.

(21) Appl. No.: 12/737,057

(22) PCT Filed: Sep. 4, 2009

(86) PCT No.: PCT/JP2009/065525
§ 371 (c)(1),
(2), (4) Date: Dec. 6, 2010

(87) PCT Pub. No.: WO2010/029898
PCT Pub. Date: Mar. 18, 2010

(65) Prior Publication Data
US 2012/0013579 A1    Jan. 19, 2012

(30) Foreign Application Priority Data
Sep. 10, 2008 (JP) ................................. 2008-231625

(51) Int. Cl.
*A61B 3/02* (2006.01)
(52) U.S. Cl. ........................ 351/224; 351/237
(58) Field of Classification Search .......... 351/224–226, 351/237
See application file for complete search history.

(56) References Cited

U.S. PATENT DOCUMENTS

| | | | |
|---|---|---|---|
| 2007/0159598 A1* | 7/2007 | Yancey et al. | 351/206 |
| 2008/0278682 A1* | 11/2008 | Huxlin et al. | 351/203 |
| 2011/0122367 A1* | 5/2011 | Tsuta | 351/224 |
| 2011/0176112 A1* | 7/2011 | Tsuta | 351/224 |
| 2011/0273670 A1* | 11/2011 | Tsuta | 351/224 |
| 2012/0038596 A1* | 2/2012 | Tsuta | 345/204 |

FOREIGN PATENT DOCUMENTS

| | | |
|---|---|---|
| JP | S58/121937 | 7/1983 |
| JP | H4/135534 | 5/1992 |
| JP | H14/306413 | 10/2002 |
| JP | H16/73545 | 3/2004 |
| JP | H19/29112 | 2/2007 |
| JP | H19/75350 | 3/2007 |
| JP | H20/36297 | 2/2008 |
| WO | WO-2006-106877 | 10/2006 |

* cited by examiner

*Primary Examiner* — Jordan Schwartz

(57) ABSTRACT

A method for static visual field scanning apparatus including: a step of visual field scanning screen generating means; step of scanning region setting means; step of fixation image displaying and controlling means; step of scan line setting means; step of scanning point setting means; step of visual target displaying and controlling means; step of the first detection means; step of the second detection means; step of visual field mapping screen generating means; step of immediate post first detection scan continuation means; step of immediate post second detection scan continuation means; step of visual target display coordinates storing means; step of visual target perception inability symbol mapping means; step of the first completion judgement means; step of the second completion judgement means; step of post first completion judgement the next scanning point calculation means; and step of post second completion judgement the next scanning point calculation means.

2 Claims, 11 Drawing Sheets

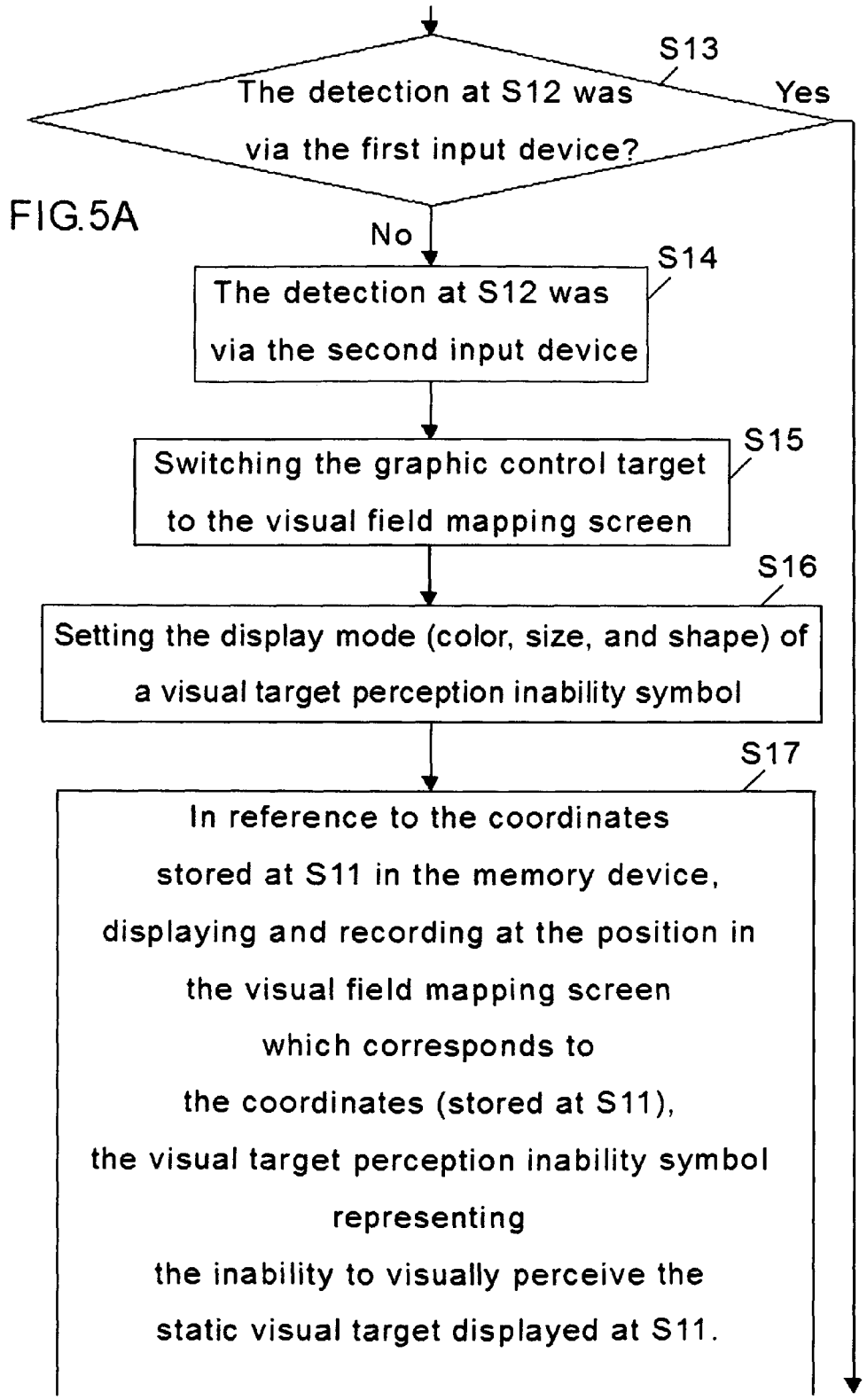

That is, at the position of the x coordinate of stcounxv+counxv (dots)

and the y coordinate of stcounyv+counyv (dots)

in the visual field mapping screen, displaying and recording the symbol which represents the inability to perceive the static visual target at the corresponding position of the visual field scanning screen.

Switching the graphic control target to the visual field scanning screen — S18

FIG.5B counx ← counx+1
counxv ← counx*5    S19 stcounxvz ← stcounxv+counxv    S20

METHOD FOR STATIC VISUAL FIELD SCANNING APPARATUS

BACKGROUND OF THE INVENTION

The present invention relates to a static visual field scanning apparatus, a method for a static visual field scanning apparatus, a program for realizing a static visual field scanning apparatus, and a computer-readable recorded medium. Previous perimeters include: Goldmann perimeter model 510 [1945] and model 940 [1967]; Tubinger perimeter [1957]; and Octopus perimeter [1976].
(See, e.g., the non-patent literature 1.)
The previous perimeters are explained:
Goldmann perimeter is the first brightness perimeter, adopting the method of simultaneous manual recording, with 4 to 60 degrees of brightness of the visual target and 6 types of visual angle of the visual target, capable of examining visual field of visual angle, and with adjustability of its background brightness. The shortcoming is that it fails to examine the central region within 5 degrees;

Tubinger perimeter [1957] is the first practical static perimeter, capable of examining the kinetic visual field and the visual field of color, flicker, and etc., adopting the method of simultaneous manual recording, with 80 degrees of brightness of the visual target and 100 degrees of brightness of the fixation image and 5 kinds of color and 6 degrees of background brightness, and capable of examining the central and eccentric vision. Its shortcoming is in the difficulty of controlling the visual target movement, and of adjusting the visual target, fixation image, and background illumination lamp;

Octopus perimeter [1976] is the world's first fully automated static perimeter.
Non-patent literature 1: "The latest comprehensive dictionary of medical science", Ishiyaku Publishers Inc., 1987, 1990.
Previous perimeters take long time in the examination.
The shapes of scotoma and blind spot detected by previous perimeters are very rough and the charts obtained from the examinations greatly differ from the true reflection of the shapes of scotoma and blind for the subjects. Previous perimeters have failed to detect visual field impairments of early stages.

The aim of the present invention is, therefore, to provide a static visual field scanning apparatus that employs the structure and operational aspect which allow for the maximum reduction of the redundancy such as waits, repetitive examinations, etc. frequently caused by previous perimeters, and realizing speeding the examination.

The aim of the present invention is also to provide a static visual field scanning apparatus capable of reflecting, in much greater detail, the shape of scotoma and blind spot true to a subject into the image obtained by the examination.

SUMMARY OF THE INVENTION

To achieve the above aim,
The invention of claim 1 is an operational method for a static visual field scanning apparatus including:

A step of means for generating, on an output device, a visual field scanning screen for scanning a visual field of a subject using a static visual target;

A step of means for setting an area to be scanned by the static visual target, as a scanning region, on the visual field scanning screen that is generated, on the output device, by said step of visual field scanning screen generating means;

A step of means for displaying and controlling a fixation image to be fixated by the subject, during a visual field scanning, on the visual field scanning screen generated by said step of visual field scanning screen generating means;

A step of means for setting at least one scan line on said visual field scanning screen;

A step of means for setting at least one scanning point along the scan line set by said step of scan line setting means;

A step of means for displaying and controlling the static visual target at a scanning point among the scanning points, to scan the visual field corresponding to said scanning point, which are set, along the scan line, by said step of scanning point setting means;

A step of means for detecting the response to be made, via a first input device, at the time when the static visual target, displayed by said step of visual target displaying and controlling means, is perceived;

A step of means for detecting the response to be made, via a second input device, at the time when the static visual target, displayed by said step of visual target displaying and controlling means, cannot be perceived;

A step of means for generating a visual field mapping screen, on an output device, to map and display the subject's visual field;

A step of means, through said step of visual target displaying and controlling means, for continuing the scan of the visual field corresponding to a next scanning point by displaying the static visual target to scan the visual field corresponding to the next scanning point, at the next scanning point among the scanning points set by said step of scanning point setting means, immediately after stopping displaying, promptly when detecting the response via said first input device through said step of the first detection means, the static visual target displayed by said step of visual target displaying and controlling means at the time of said detection;

A step of means, through said step of visual target displaying and controlling means, for continuing the scan of the visual field corresponding to a next scanning point by displaying the static visual target to scan the visual field corresponding to the next scanning point, at the next scanning point among the scanning points set by said step of scanning point setting means, immediately after stopping displaying, promptly when detecting the response via said second input device through said step of the second detection means, the static visual target displayed by said step of visual target displaying and controlling means at the time of said detection;

A step of means for storing in a memory device the coordinates of the static visual target displayed, either at the time of the response via said first input device being detected through said step of the first detection means or at the time of the response via said second input device being detected through said step of the second detection means, by said step of visual target displaying and controlling means;

A step of means for, when the response via said second input device is detected by said step of the second detection means, recording, in reference to the coordinates stored in the memory device at the time of said detection by said step of visual target display coordinates storing means, at a position of said visual field mapping screen which corresponds to said coordinates, a symbol which represents the inability to visually perceive the static visual target displayed at said coordinates by said step of visual target displaying and controlling means;

A step of means, through said step of immediate post first detection scan continuation means, for, when the response via said first input device is detected by said step of the first detection means, making a judgement, using an arithmetic unit, about whether the scan of the scanning points along a scan line which the static visual target displayed by said step of visual target displaying and controlling means at the time of said detection, belonged to and lay at has been completed or not;

A step of means, through said step of immediate post second detection scan continuation means, for, when the response via said second input device is detected by said step of the second detection means, making a judgement, using the arithmetic unit, about whether the scan of the scanning points along a scan line which the static visual target displayed by said step of visual target displaying and controlling means at the time of said detection, belonged to and lay at has been completed or not;

A step of means, through said step of immediate post first detection scan continuation means, for, when the scan of the scanning points on a scan line is judged to be uncompleted by said step of the first completion judgement means, designating through the calculation of the arithmetic unit as the next scanning point the scanning point that shares the scan line with, and is adjacent to, the static visual target displayed at the time of the response via said first input device being detected through said step of the first detection means, by said step of visual target displaying and controlling means, and for, when the scan of the scanning points on a scan line is judged to be completed by said step of the first completion judgement means, through the calculation of the arithmetic unit, switching the scan line for scanning to the scan line adjacent to the scan line which the static visual target displayed by said step of visual target displaying and controlling means at the time of the response, via said first input device, being detected through said step of the first detection means, belonged to and lay at, and designating as the next scanning point the scanning point that lies in an edge of said scan line;

And a step of means, through said step of immediate post second detection scan continuation means, for, when the scan of the scanning points on a scan line is judged to be uncompleted by said step of the second completion judgement means, designating through the calculation of the arithmetic unit as the next scanning point the scanning point that shares the scan line with, and is adjacent to, the static visual target displayed at the time of the response via said second input device being detected through said step of the second detection means, by said step of visual target displaying and controlling means, and for, when the scan of the scanning points on a scan line is judged to be completed by said step of the second completion judgement means, through the calculation of the arithmetic unit, switching the scan line for scanning to the scan line adjacent to the scan line which the static visual target displayed by said step of visual target displaying and controlling means at the time of the response, via said second input device, being detected through said step of the second detection means, belonged to and lay at, and designating as the next scanning point the scanning point that lies in an edge of said scan line.

The invention of claim 2 is a computer-readable recorded medium recording a program for causing a computer to realize the function including:

Means for generating, on an output device, a visual field scanning screen for scanning a visual field of a subject using a static visual target;

Means for setting an area to be scanned by the static visual target, as a scanning region, on the visual field scanning screen that is generated, on the output device, by said visual field scanning screen generating means;

Means for displaying and controlling a fixation image to be fixated by the subject, during a visual field scanning, on the visual field scanning screen generated by said visual field scanning screen generating means;

Means for setting at least one scan line on said visual field scanning screen;

Means for setting at least one scanning point along the scan line set by said scan line setting means;

Means for displaying and controlling the static visual target at a scanning point among the scanning points, to scan the visual field corresponding to said scanning point, which are set, along the scan line, by said scanning point setting means;

Means for detecting the response to be made, via a first input device, at the time when the static visual target, displayed by said visual target displaying and controlling means, is perceived;

Means for detecting the response to be made, via a second input device, at the time when the static visual target, displayed by said visual target displaying and controlling means, cannot be perceived;

Means for generating a visual field mapping screen, on an output device, to map and display the subject's visual field;

Means, through said visual target displaying and controlling means, for continuing the scan of the visual field corresponding to a next scanning point by displaying the static visual target to scan the visual field corresponding to the next scanning point, at the next scanning point among the scanning points set by said scanning point setting means, immediately after stopping displaying, promptly when detecting the response via said first input device through said first detection means, the static visual target displayed by said visual target displaying and controlling means at the time of said detection;

Means, through said visual target displaying and controlling means, for continuing the scan of the visual field corresponding to a next scanning point by displaying the static visual target to scan the visual field corresponding to the next scanning point, at the next scanning point among the scanning points set by said scanning point setting means, immediately after stopping displaying, promptly when detecting the response via said second input device through said second detection means, the static visual target displayed by said visual target displaying and controlling means at the time of said detection;

Means for storing in a memory device the coordinates of the static visual target displayed, either at the time of the response via said first input device being detected through said first detection means or at the time of the response via said second input device being detected through said second detection means, by said visual target displaying and controlling means;

Means for, when the response via said second input device is detected by said second detection means, recording, in reference to the coordinates stored in the memory device at the time of said detection by said visual target display coordinates storing means, at a position of said visual field mapping screen which corresponds to said coordinates, a symbol which represents the inability to visually perceive the static visual target displayed at said coordinates by said visual target displaying and controlling means;

Means, through said immediate post first detection scan continuation means, for, when the response via said first input device is detected by said first detection means, making a judgement, using an arithmetic unit, about whether the scan of the scanning points along a scan line which the static visual target displayed by said visual target displaying and controlling means at the time of said detection, belonged to and lay at has been completed or not;

Means, through said immediate post second detection scan continuation means, for, when the response via said second input device is detected by said second detection means, making a judgement, using the arithmetic unit, about whether the scan of the scanning points along a scan line which the static visual target displayed by said visual target displaying and controlling means at the time of said detection, belonged to and lay at has been completed or not;

Means, through said immediate post first detection scan continuation means, for, when the scan of the scanning points on a scan line is judged to be uncompleted by said first completion judgement means, designating through the calculation of the arithmetic unit as the next scanning point the scanning point that shares the scan line with, and is adjacent to, the static visual target displayed at the time of the response via said first input device being detected through said first detection means, by said visual target displaying and controlling means, and for, when the scan of the scanning points on a scan line is judged to be completed by said first completion judgement means, through the calculation of the arithmetic unit, switching the scan line for scanning to the scan line adjacent to the scan line which the static visual target displayed by said visual target displaying and controlling means at the time of the response, via said first input device, being detected through said first detection means, belonged to and lay at, and designating as the next scanning point the scanning point that lies in an edge of said scan line;

And means, through said immediate post second detection scan continuation means, for, when the scan of the scanning points on a scan line is judged to be uncompleted by said second completion judgement means, designating through the calculation of the arithmetic unit as the next scanning point the scanning point that shares the scan line with, and is adjacent to, the static visual target displayed at the time of the response via said second input device being detected through said second detection means, by said visual target displaying and controlling means, and for, when the scan of the scanning points on a scan line is judged to be completed by said second completion judgement means, through the calculation of the arithmetic unit, switching the scan line for scanning to the scan line adjacent to the scan line which the static visual target displayed by said visual target displaying and controlling means at the time of the response, via said second input device, being detected through said second detection means, belonged to and lay at, and designating as the next scanning point the scanning point that lies in an edge of said scan line.

The static visual field scanning apparatus of the present invention employing the structure and operational aspect which allow for the maximum reduction of the redundancy arising in previous perimeters is prominently light in its operation and capable of scanning a very larger amount of scanning points within a predetermined time using the static visual target.

So, the examination detailed and quick compared with those of previous perimeters can be realized.

As explicitly shown in FIG. 1 and FIG. 8 that are examples of the visual field mapping image generated by a static visual field scanning apparatus of the present invention, the static visual field scanning apparatus of the present invention can map not only the forms of a scotoma 201 and a blind spot 203, but also the form of a connection of scotoma to blind spot 202 in detail.

The static visual field scanning apparatus of the present invention can generate, from the data obtained by its static visual field scanning, the visual field mapping image proper for being called scan of static visual field, strongly indicating the retinal structure and so forth.

The static visual field scanning apparatus of the present invention may be embodied by a simple setup without the need for voluminous equipment such as Goldmann perimeter or the like.

The static visual field scanning apparatus of the present invention can examine the central portion within 5 degrees of the visual field.

So, according to the first invention of an operational method for a static visual field scanning apparatus, the visual field mapping image, for example, as shown in FIG. 1 and FIG. 8 can be obtained by the static visual field scanning.

The operational method for a static visual field scanning apparatus of the present invention employs the structure and operational aspect which allow for the maximum reduction of the redundancy arising in previous perimeters, and is prominently light in its operation and, therefore, realizes the scan of a very larger amount of scanning points within a predetermined time using the static visual target.

So, according to the second invention of a computer-readable recorded medium which records a program for realizing a static visual field scanning apparatus, the visual field mapping image, for example, as shown in FIG. 1 and FIG. 8 can be obtained by the static visual field scanning of the static visual field scanning apparatus that can be realized by loading into a computer and carrying out the program for realizing a static visual field scanning apparatus.

The operational method for a static visual field scanning apparatus of the present invention employs the structure and operational aspect which allow for the maximum reduction of the redundancy arising in previous perimeters, and is prominently light in its operation and, therefore, realizes the scan of a very larger amount of scanning points within a predetermined time using the static visual target.

BRIEF DESCRIPTION OF THE DRAWINGS

FIG. 5A is a continued flow chart showing a preferred embodiment of the static visual field scanning and visual field mapping process of the present invention of a static visual field scanning apparatus.

FIG. 5B is a continued flow chart showing a preferred embodiment of the static visual field scanning and visual field mapping process of the present invention of a static visual field scanning apparatus.

DETAILED DESCRIPTION OF THE INVENTION

Figure 1:
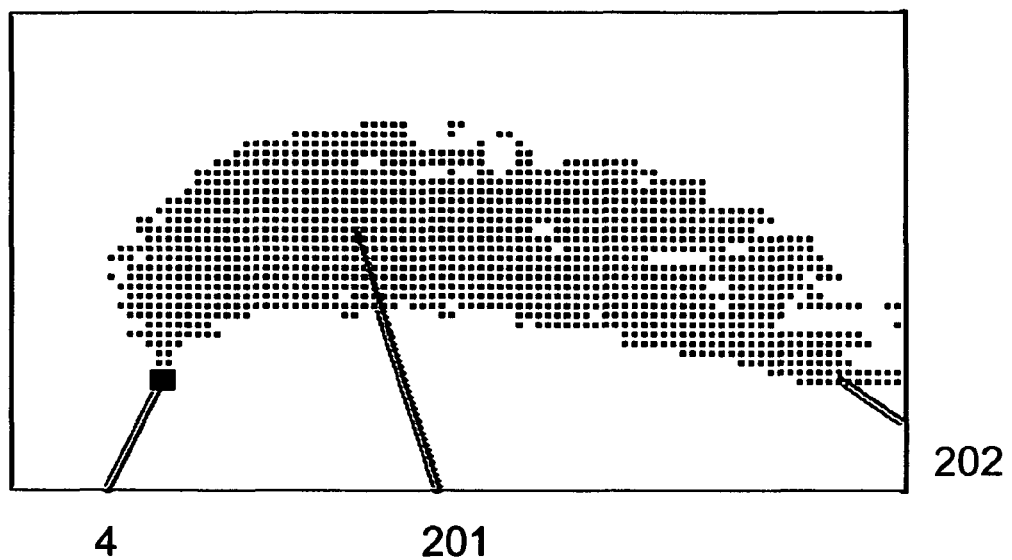
FIG. 1 is an image demonstrating an embodiment of the visual field mapping image generated by a preferred scanning of the present invention of a static visual field scanning apparatus.

The detailed explanation of the present invention of a static visual field scanning apparatus, a method for a static visual field scanning apparatus, a program for realizing a static visual field scanning apparatus, and a computer-readable recorded medium will be disclosed as below while referring to the drawings.

Figure 3:
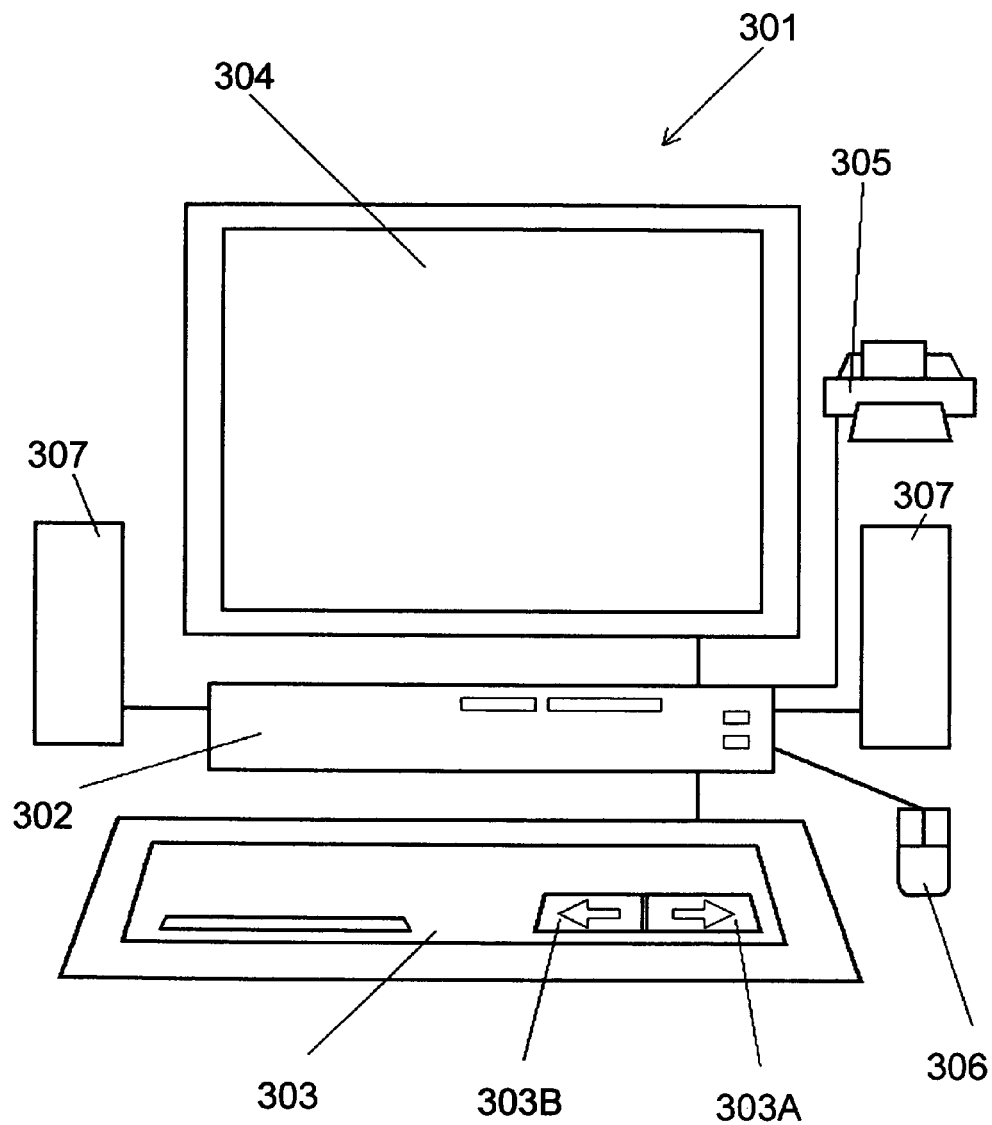
FIG. 3 is a diagram showing a preferred embodiment of the system of the present invention of a static visual field scanning apparatus.
Figure 4A:
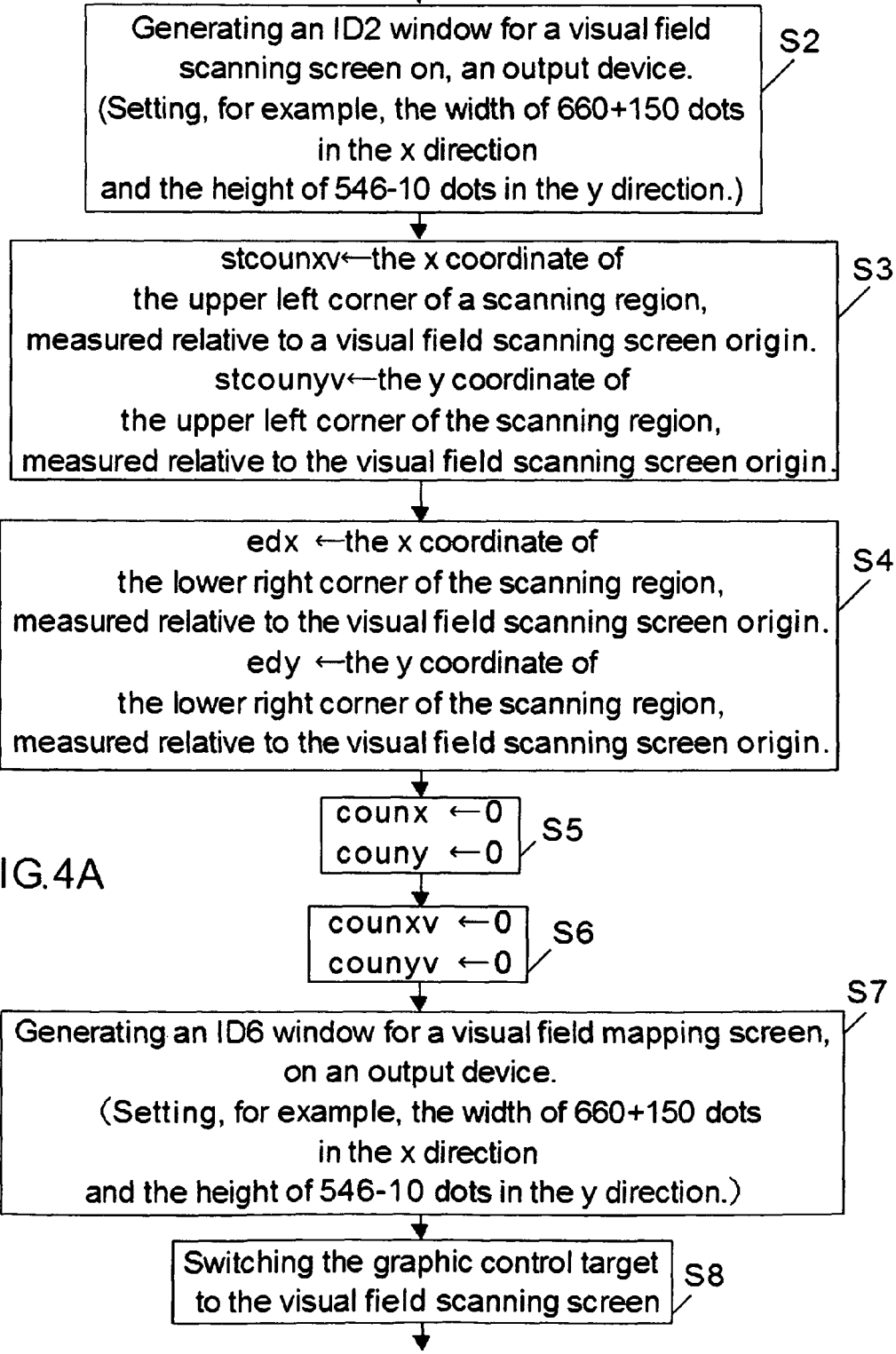
FIG. 4A is a flow chart showing a preferred embodiment of the static visual field scanning and visual field mapping process of the present invention of a static visual field scanning apparatus.
Figure 4B:
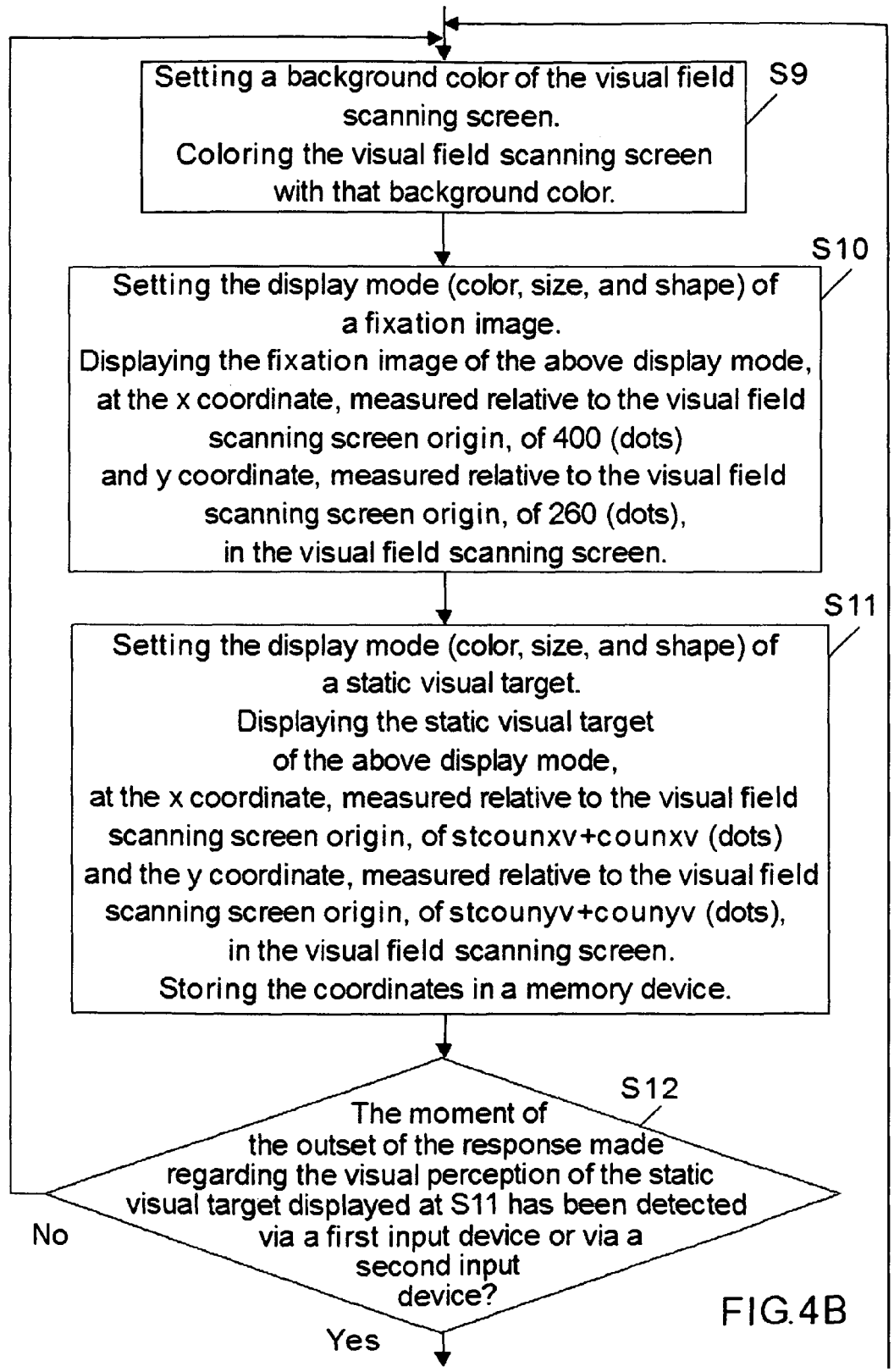
FIG. 4B is a continued flow chart showing a preferred embodiment of the static visual field scanning and visual field mapping process of the present invention of a static visual field scanning apparatus.
Figure 6:
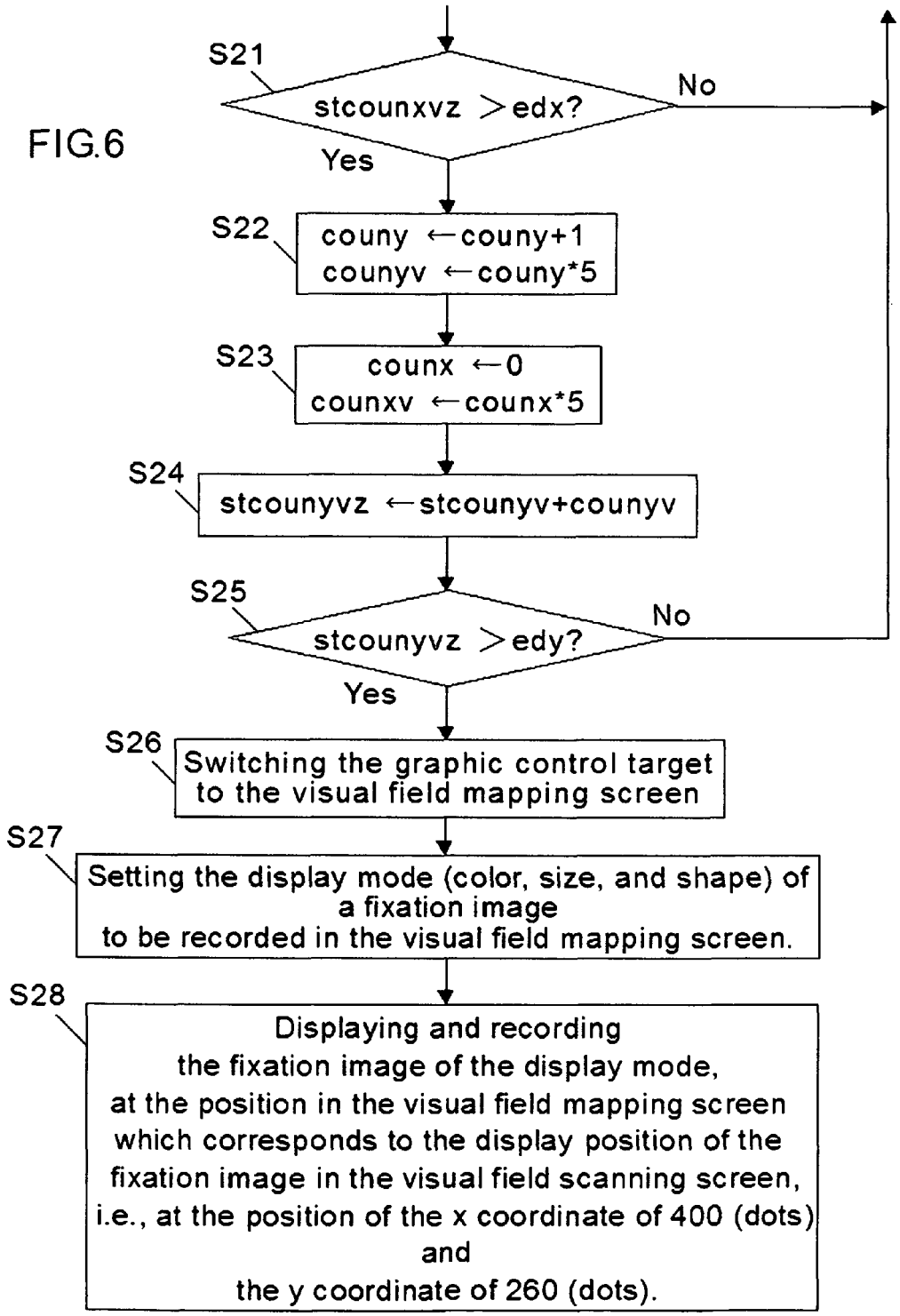
FIG. 6 is a continued flow chart showing a preferred embodiment of the static visual field scanning and visual field mapping process of the present invention of a static visual field scanning apparatus.
Figure 7:
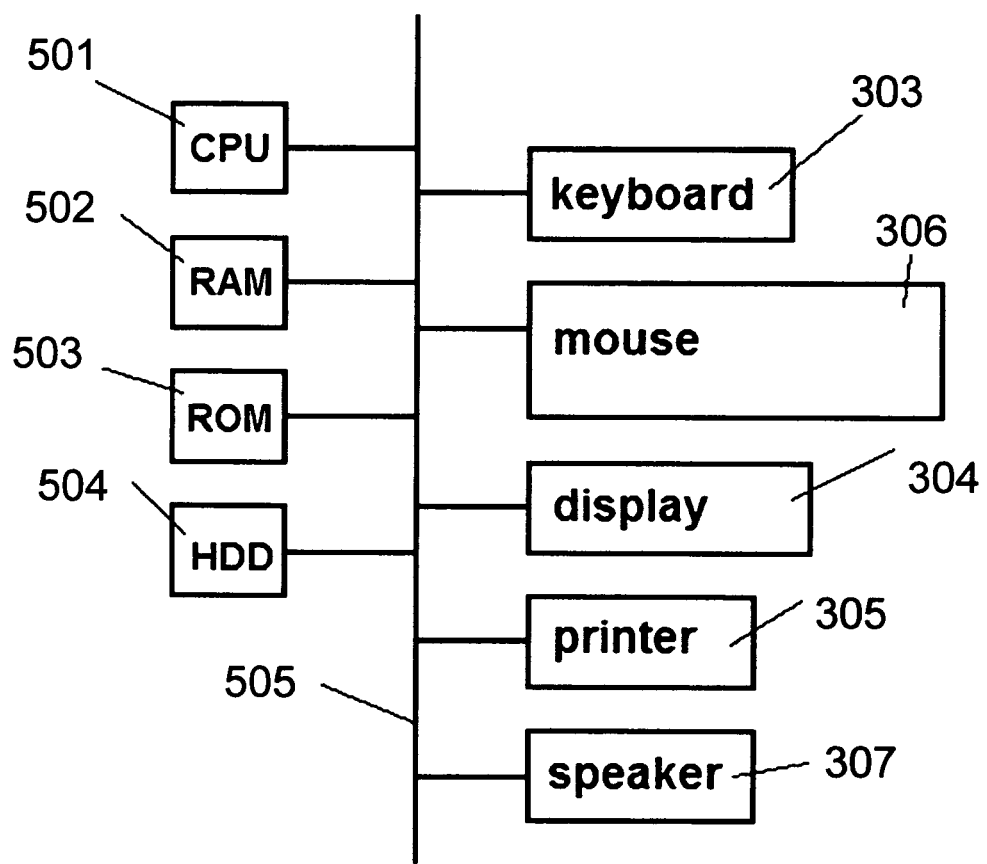
FIG. 7 is a block diagram showing a preferred embodiment of the hardware configuration of a CPU in the present invention of a static visual field scanning apparatus.
Figure 8:
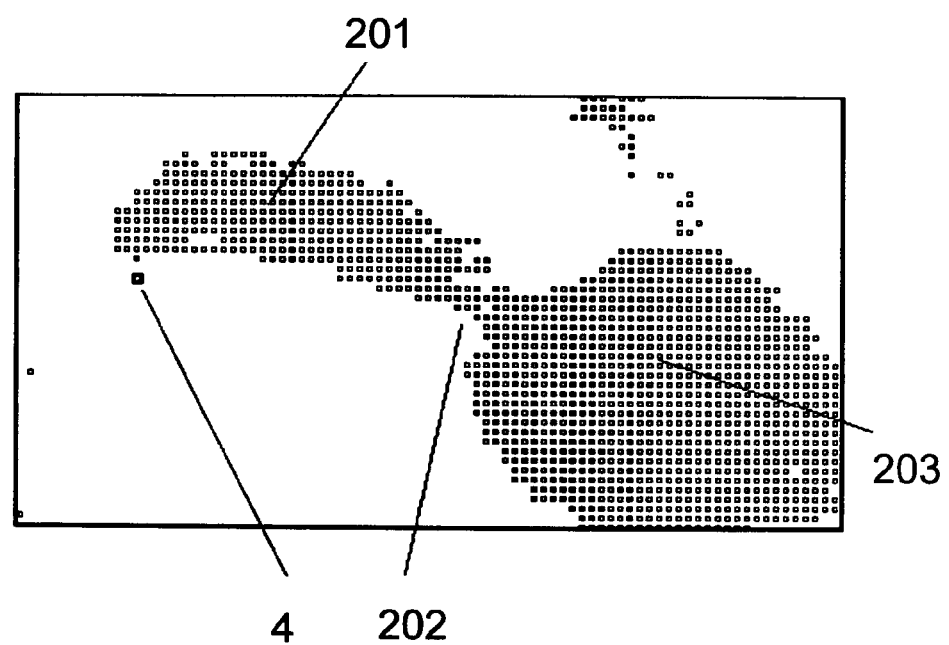
FIG. 8 is an image demonstrating an embodiment of the visual field mapping image generated by a preferred scanning of the present invention of a static visual field scanning apparatus.

Firstly, a setup of the present invention of the perimeter is described referring to FIG. 3 and FIG. 7.

FIG. 3 shows an embodiment of the system of the present invention of a static visual field scanning apparatus.

FIG. 7 shows an embodiment of the hardware configuration of a CPU 501 in the present invention of a static visual field scanning apparatus.

FIG. 3 shows a computer system 301 diagrammatically.

The present invention of a static visual field scanning apparatus is realized by the computer system 301 carrying out a program for realizing the static visual field scanning apparatus.

As shown in FIG. 3, the computer system 301 realizing an embodiment of the present invention of a static visual field scanning apparatus includes a main unit 302 that is equipped with a CPU (Central Processing Unit) 501, etc., which will be mentioned later, a keyboard 303, (if necessary, a mouse 306), a display 304, and a printer 305 (and if necessary, a speaker 307 too).

Next, an embodiment of the hardware configuration of the CPU 501 in the present invention of a static visual field scanning apparatus is described referring to FIG. 7.

The CPU 501 in the present invention of a static visual field scanning apparatus is configured specifically including:
a microprocessor such as the CPU 501, a RAM (Random Access Memory) 502, a ROM (Read Only Memory) 503, a HDD (Hard Disc Drive) 504, a keyboard 303, a mouse 306, a display 304, a printer 305, a speaker 307, and a communications interface.

These parts are connected via a bus 505.

(The HDD 504 is connected through the input-output interface to the bus 505.)

The keyboard 303 is connected through the input-output interface to the bus 505, which enables output to the CPU 501 of input by the keyboard 303.

The display 304 is connected through the input-output interface to the bus 505, which enables output to the display 304 of image data input from the CPU 501.

The printer 305 is connected through the input-output interface to the bus 505, which enables output by the printer 305 of input from the CPU 501.

(The speaker 307 is connected through the input-output interface to the bus 505, which enables output by the speaker 307 of input from the CPU 501.)

(The mouse 306 is connected through the input-output interface to the bus 505, which enables output to the CPU 501 of input through the mouse 306.)

The CPU 501 carries out operations characteristic of an embodiment of the present invention, by loading onto the RAM 502 a program, which is stored in the HDD (Hard Disc Drive) 504, for realizing the present invention of a static visual field scanning apparatus.

The CPU 501 carries out controls, and kinds of arithmetic processing, of the present invention of a static visual field scanning apparatus, according to a program for realizing the present invention of a static visual field scanning apparatus.

The CPU 501 controls display processing of the display 304 (an example of the output device). (Specifically, the CPU 501, for example, displaying and controlling a fixation image and a visual target, and generating a visual field mapping image from a data obtained by the present invention of a static visual field scanning apparatus.)

The CPU 501 controls the present invention of a static visual field scanning apparatus according to input by the keyboard 303 (an example of the input device).

The CPU 501 can control the printer 305 and the like so as to output the visual field mapping image, etc. that are generated based on the data obtained from a static visual field scanning apparatus.

(If necessary,
the CPU 501 may control the speaker 307 (an example of the output device) to produce output (for example, according to input by an input device such as the keyboard 303 or the like, or, for example, when the scan line is switched in the static visual field scanning, or, for example, when the visual field mapping image is output, or the like).)

(The CPU 501 may control the present invention of a static visual field scanning apparatus according to input from the mouse 306 (an example of the input device).)

The keyboard 303 (and if necessary, the mouse 306) and the display 304 are used as user interfaces in the present invention of a static visual field scanning apparatus.

The keyboard 303 is used, for example, as a device for input (the input device).

(If necessary, the mouse 306 is used as a device for performing various kinds of operations of input to the display screen of the display 304.)

The display 304 is a display device (the output device), for example, of a LCD (Liquid Crystal Display), a CRT (Cathode Ray Tube), or the like, which scans a visual field in accordance with the present invention of a static visual field scanning apparatus, and displays a visual field mapping image generated by the present invention of a static visual field scanning apparatus.

(If necessary, various screens such as an operation screen and a setting screen may be displayed on the display 304.)

And when the CPU 501 is connected to communications network such as the Internet and a LAN (Local Area Network), the communications interface can be equipped with a network adapter such as a LAN card or communications equipment such as a modem, in order to establish data communication among the network. In such a case, by installing on the network a server storing a program for realizing the present invention of a static visual field scanning apparatus, and configuring the CPU 501 as a client terminal of the server, the operation of the present invention of a static visual field scanning apparatus can be carried out by a static visual field scanning apparatus.

A program for realizing the present invention of a static visual field scanning apparatus can be stored on any non-transitory computer-readable recording media (storage media).

Examples of such non-transitory recording media (storage media) include an optical disk, a magneto-optic disk (CD-ROM, DVD-RAM, DVD-ROM, MO, etc.), a magnetic-storage device (hard disk, Floppy Disk™, ZIP, etc.), a semiconductor memory, etc.

Next, the detailed explanation regarding the present invention of a static visual field scanning apparatus, operational method of a static visual field scanning apparatus, and program for realizing a static visual field scanning apparatus will be described while referring to FIG. 2, FIG. 4A, FIG. 5A, FIG. 5B, FIG. 6, and FIG. 9, as below.

Figure 2:
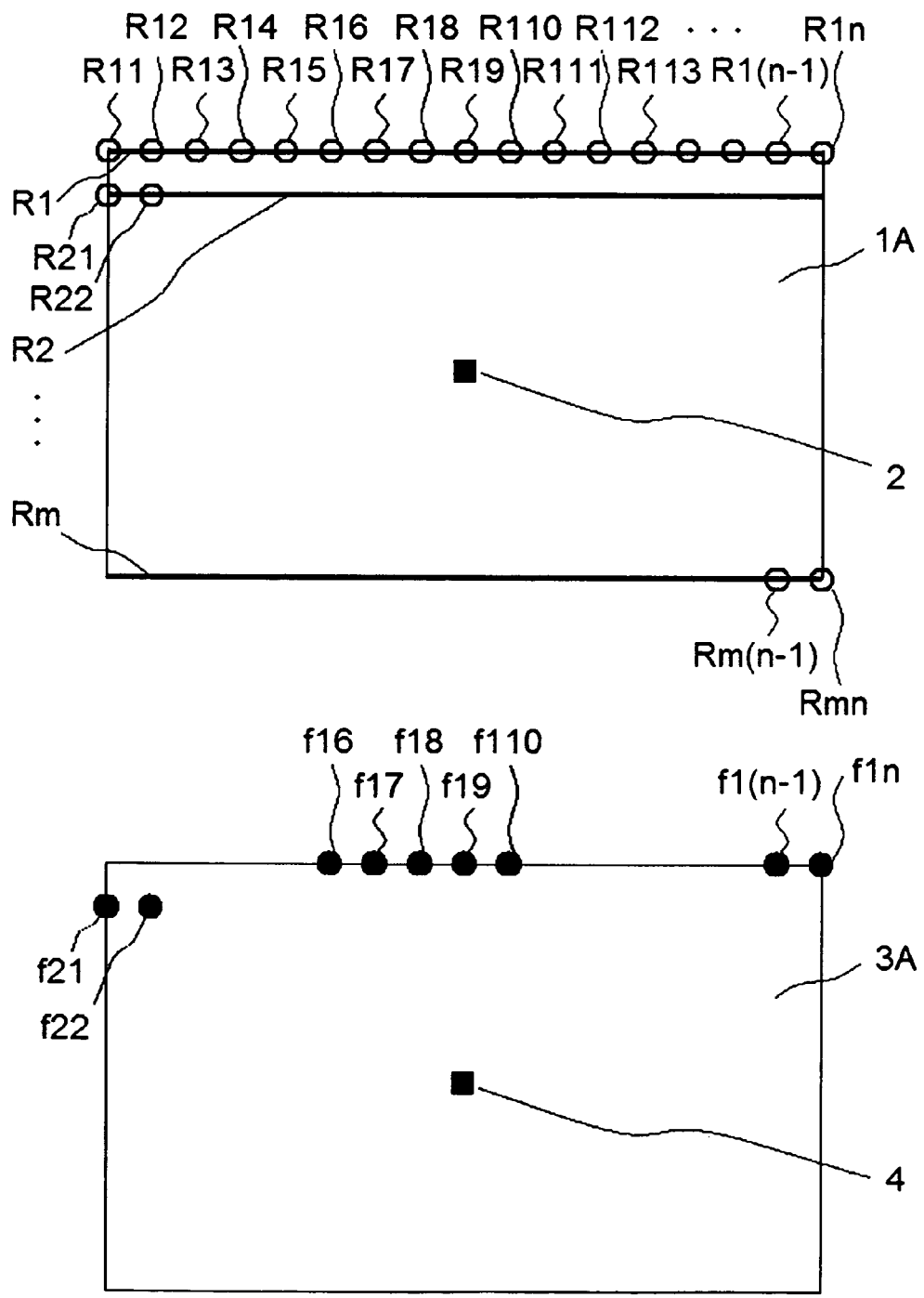
FIG. 2 is a schematic diagram showing a preferred embodiment of the scanning, operation, and visual field mapping aspect of the present invention of a static visual field scanning apparatus.

FIG. 2 shows an embodiment of the scanning, operation, and static visual field mapping aspect of the present invention of a static visual field scanning apparatus.

FIG. 4A, FIG. 4B, FIG. 5A, FIG. 5B, and FIG. 6 show an embodiment of the static visual field scanning and visual field mapping process of the present invention of a static visual field scanning apparatus.

Figure 9:
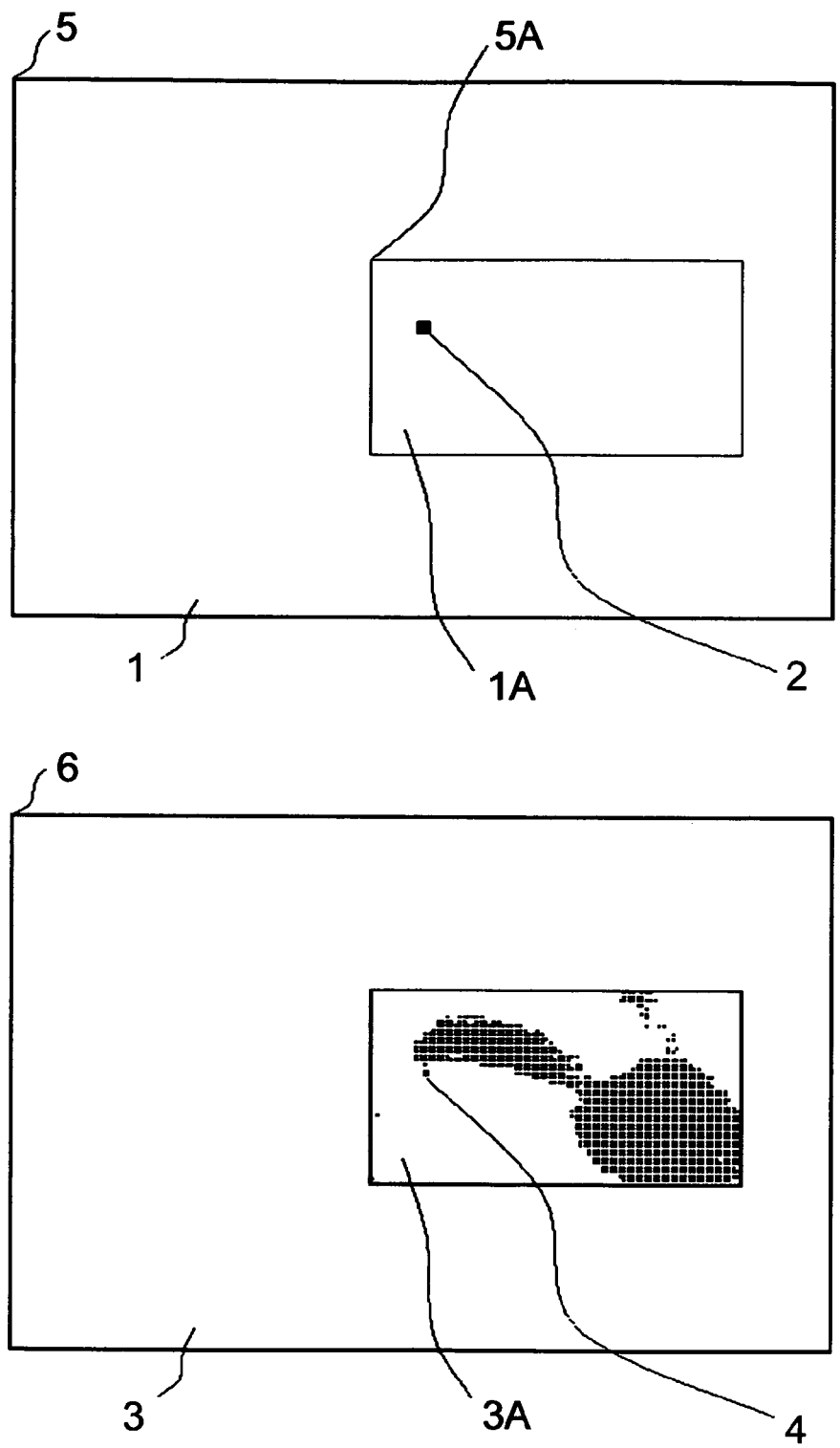
FIG. 9 is a diagram showing a preferred embodiment of the display screen of the present invention of a static visual field scanning apparatus.

FIG. 9 shows a preferred embodiment of the display screen of the present invention of a static visual field scanning apparatus.

First, referring to FIG. 2, an embodiment of the scanning, operation, and visual field mapping aspect of the present invention of a static visual field scanning apparatus is described in detail.

A CPU 501 generates a visual field scanning screen 1 on an output device (for example, a display 304). (A visual field scanning screen generating means.)

The CPU 501 displays a fixation image 2 at a predetermined position on the visual field scanning screen 1 in accordance with a program for realizing the present invention of a static visual field scanning apparatus.
(A fixation image displaying and controlling means.)

The fixation image 2 is to be fixated by an eye of a subject during static visual field scanning.

The CPU 501 sets, in a scanning region 1A set in the visual field scanning screen 1, a plurality of scan lines according to the program for realizing the present invention of a static visual field scanning apparatus. For example, the CPU 501 arranges from an upper side of the screen a scan line R1, a scan line R2, . . . , and a scan line Rm in order, each with a predetermined spacing (for example, in the y direction). (A scan line setting means.)

The CPU 501 does not display such scan lines on the visual field scanning screen 1, since each of them is set as a path along which the location of a static visual target changes in the visual field scanning.
(Although scan lines are horizontally set in FIG. 2, they may be set with other directionality.)
(A scanning region 1A may be set over the visual field scanning screen 1.)

The CPU 501 displays first, for example, a static visual target at a scanning point R11 in a left side of the scanning region 1A on the scan line R1 in accordance with the program for realizing the present invention of a static visual field scanning apparatus. (Forming a part of visual target displaying and controlling means.)

And then the CPU 501, while displaying the static visual target at the scanning point R11, waits for a response during the period in which the response via a first input device (for example, a right cursor key 303A in an embodiment of the present invention) is not detected by a first detection means and the response via a second input device (for example, a left cursor key 303B in an embodiment of the present invention) is not detected by a second detection means, in accordance with the program for realizing the present invention of a static visual field scanning apparatus. (A response waiting means.)

(In an embodiment of the present invention, the first input device is, for example, a right cursor key 303A, and the second input device is, for example, a left cursor key 303B. And in an embodiment of the present invention of a static visual field scanning apparatus, the response is made by a momentary depression of the right cursor key 303A when the static visual target displayed in the visual field scanning screen 1 can be perceived by the subject, and the response is made by a momentary depression of the left cursor key 303B when the static visual target displayed in the visual field scanning screen 1 cannot be perceived by the subject.)

(In an embodiment of the present invention, the first detection means is a means for detecting only the moment of the outset of the response made, via the first input device (for example, a right cursor key 303A in an embodiment of the present invention), when the static visual target displayed in the visual field scanning screen 1 can be perceived. That is, in an embodiment of the present invention, for example, the subject makes the response of the static visual target being perceivable, by momentary depressing the right cursor key 303A when the subject can perceive the static visual target displayed in the visual field scanning screen 1, and the first detection means carries out the operation of detecting only the moment of the outset of the depression of the right cursor key 303A, and leaving undetected the after period where the depression of the right cursor key 303A is continuing (in the momentary depression). That is, the first detection means operates to detect only the instant of the depression of the right cursor key 303A. That is, the first detection means operates to transmit the information only once of the depression when the right cursor key 303A is depressed, and after that not to transmit the information of the depression until the depressed right cursor key 303A is released.)

(In an embodiment of the present invention, the second detection means is a means for detecting only the moment of the outset of the response made, via the second input device (for example, a left cursor key 303B in an embodiment of the present invention), when the static visual target displayed in the visual field scanning screen 1 cannot be perceived. That is, in an embodiment of the present invention, for example, the subject makes the response of the static visual target being unperceivable, by momentary depressing the left cursor key 303B when the subject cannot perceive the static visual target displayed in the visual field scanning screen 1, and the second detection means carries out the operation of detecting only the moment of the outset of the depression of the left cursor key 303B, and leaving undetected the after period where the depression of the left cursor key 303B is continuing (in the momentary depression). That is, the second detection means operates to detect only the instant of the depression of the left cursor key 303B. That is, the second detection means operates to transmit the information only once of the depression when the left cursor key 303B is depressed, and after that not to transmit the information of the depression until the depressed left cursor key 303B is released.)

Suppose now that the subject who fixates the fixation image 2 can visually perceive the static visual target displayed at the scanning point R11.

The subject makes, at the time when the subject was able to visually perceive in the visual field the static visual target displayed at the scanning point R11, the response of the static visual target being perceivable (for example, the momentary depression of the right cursor key 303A in an embodiment of the present invention), via the first input device (for example, the right cursor key 303A in an embodiment of the present invention).

The CPU 501 continues the scan of the visual field corresponding to a next scanning point (a scanning point R12) by displaying the static visual target to scan the visual field corresponding to the next scanning point (the scanning point R12), at the next scanning point (i.e., the scanning point R12), immediately after stopping displaying, promptly when detecting the response via the first input device (for example, the right cursor key 303A in an embodiment of the present invention) through the first detection means (in this case, the response made by the subject of the static visual target displayed at the scanning point R11 being perceivable in the visual field), the displayed static visual target (the static visual target displayed at the scanning point R11). (Forming a part of visual target displaying and controlling means.)

(An immediate post first detection scan continuation means.) (In this instance, the next scanning point (the scanning point R12) is determined by a first completion judgement means and a post first completion judgement the next scanning point calculation means.)

(That is, the CPU 501, after detecting the response via the first input device (for example, the right cursor key 303A in an embodiment of the present invention) through the first detection means (in this case, the response made by the subject of the static visual target displayed at the scanning point R11 being perceivable in the visual field), makes a judgement, using an arithmetic unit, about whether the scan of the scanning points along the scan line (i.e., the scan line R1) which the static visual target displayed in the visual field scanning screen 1 at the time of the detection (the static visual target displayed at the scanning point R11), belonged to and lay at has been completed or not (whether the scan along the scan line R1 has been completed up to the scanning point R1n or not). (A first completion judgement means.)

(In this instance, the CPU 501 makes a judgement that the scan of the scanning points on the scan line (the scan line R1) (the scan up to the scanning point R1n) is uncompleted, and designates through the calculation of the arithmetic unit as the next scanning point the scanning point (the scanning point R12) that shares the scan line (the scan line R1) with, and is adjacent to, the static visual target displayed at the time of the response via the first input device (for example, the right cursor key 303A in an embodiment of the present invention) being detected through the first detection means (the static visual target displayed at the scanning point R11).) (A post first completion judgement the next scanning point calculation means.)

(In an embodiment of the present invention of a static visual field scanning apparatus, even, for example, if the subject were holding down the right cursor key 303A, the scanning point as the next scanning point will not move from the scanning point R12 to the scanning point R13 and to the scanning point R14, . . . , etc., for example. The scanning point operates to move only once to one depression of the right cursor key 303A.)

The CPU 501 displays now, for example, a static visual target at a scanning point R12 in accordance with the program for realizing the present invention of a static visual field scanning apparatus. (Forming a part of visual target displaying and controlling means.)

And then the CPU 501, while displaying the static visual target at the scanning point R12, waits for a response during the period in which the response via the first input device (for example, the right cursor key 303A in an embodiment of the present invention) is not detected by the first detection means and the response via the second input device (for example, the left cursor key 303B in an embodiment of the present invention) is not detected by the second detection means, in accordance with the program for realizing the present invention of a static visual field scanning apparatus. (A response waiting means.)

Suppose now that the subject who fixates the fixation image 2 can visually perceive the static visual target displayed at the scanning point R12 as well.

The subject makes, at the time when the subject was able to visually perceive in the visual field the static visual target displayed at the scanning point R12, the response of the static visual target being perceivable (for example, the momentary depression of the right cursor key 303A in an embodiment of the present invention), via the first input device (for example, the right cursor key 303A in an embodiment of the present invention).

The CPU 501 continues the scan of the visual field corresponding to a next scanning point (a scanning point R13) by displaying the static visual target to scan the visual field corresponding to the next scanning point (the scanning point R13), at the next scanning point (i.e., the scanning point R13), immediately after stopping displaying, promptly when detecting the response via the first input device (for example, the right cursor key 303A in an embodiment of the present invention) through the first detection means (in this case, the response made by the subject of the static visual target displayed at the scanning point R12 being perceivable in the visual field), the displayed static visual target (the static visual target displayed at the scanning point R12). (Forming a part of visual target displaying and controlling means.)

(An immediate post first detection scan continuation means.) (In this instance, the next scanning point (the scanning point R13) is determined by the first completion judgement means and the post first completion judgement the next scanning point calculation means.)

(That is, the CPU 501, after detecting the response via the first input device (for example, the right cursor key 303A in an embodiment of the present invention) through the first detection means (in this case, the response made by the subject of the static visual target displayed at the scanning point R12 being perceivable in the visual field), makes a judgement, using the arithmetic unit, about whether the scan of the scanning points along the scan line (i.e., the scan line R1) which the static visual target displayed in the visual field scanning screen 1 at the time of the detection (the static visual target displayed at the scanning point R12), belonged to and lay at has been completed or not (whether the scan along the scan line R1 has been completed up to the scanning point R1n or not). (A first completion judgement means.)

(In this instance, the CPU 501 makes a judgement that the scan of the scanning points on the scan line (the scan line R1) (the scan up to the scanning point R1n) is uncompleted, and designates through the calculation of the arithmetic unit as the next scanning point the scanning point (the scanning point R13) that shares the scan line (the scan line R1) with, and is adjacent to, the static visual target displayed at the time of the response via the first input device (for example, the right cursor key 303A in an embodiment of the present invention) being detected through the first detection means (the static visual target displayed at the scanning point R12).) (A post first completion judgement the next scanning point calculation means.)

The CPU 501 displays now, for example, a static visual target at a scanning point R13 in accordance with the program for realizing the present invention of a static visual field scanning apparatus. (Forming a part of visual target displaying and controlling means.)

And then the CPU 501, while displaying the static visual target at the scanning point R13, waits for a response during the period in which the response via the first input device (for example, the right cursor key 303A in an embodiment of the present invention) is not detected by the first detection means and the response via the second input device (for example, the left cursor key 303B in an embodiment of the present invention) is not detected by the second detection means, in accordance with the program for realizing the present invention of a static visual field scanning apparatus. (A response waiting means.)

Suppose now that the subject who fixates the fixation image 2 can visually perceive the static visual target displayed at the scanning point R13 as well.

The subject makes, at the time when the subject was able to visually perceive in the visual field the static visual target displayed at the scanning point R13, the response of the static visual target being perceivable (for example, the momentary depression of the right cursor key 303A in an embodiment of the present invention), via the first input device (for example, the right cursor key 303A in an embodiment of the present invention).

The CPU 501 continues the scan of the visual field corresponding to a next scanning point (a scanning point R14) by displaying the static visual target to scan the visual field corresponding to the next scanning point (the scanning point R14), at the next scanning point (i.e., the scanning point R14), immediately after stopping displaying, promptly when detecting the response via the first input device (for example, the right cursor key 303A in an embodiment of the present invention) through the first detection means (in this case, the response made by the subject of the static visual target displayed at the scanning point R13 being perceivable in the visual field), the displayed static visual target (the static visual target displayed at the scanning point R13). (Forming a part of visual target displaying and controlling means.)
(An immediate post first detection scan continuation means.)
(In this instance, the next scanning point (the scanning point R14) is determined by the first completion judgement means and the post first completion judgement the next scanning point calculation means. (Like the case where the scanning point R12 was determined as a next scanning point and like the case where the scanning point R13 was determined as a next scanning point, as mentioned above.))

The CPU 501 displays now, for example, a static visual target at a scanning point R14 in accordance with the program for realizing the present invention of a static visual field scanning apparatus. (Forming a part of visual target displaying and controlling means.)

And then the CPU 501, while displaying the static visual target at the scanning point R14, waits for a response during the period in which the response via the first input device (for example, the right cursor key 303A in an embodiment of the present invention) is not detected by the first detection means and the response via the second input device (for example, the left cursor key 303B in an embodiment of the present invention) is not detected by the second detection means, in accordance with the program for realizing the present invention of a static visual field scanning apparatus. (A response waiting means.)

Suppose now that the subject who fixates the fixation image 2 can visually perceive the static visual target displayed at the scanning point R14 as well.

The subject makes, at the time when the subject was able to visually perceive in the visual field the static visual target displayed at the scanning point R14, the response of the static visual target being perceivable (for example, the momentary depression of the right cursor key 303A in an embodiment of the present invention), via the first input device (for example, the right cursor key 303A in an embodiment of the present invention).

The CPU 501 continues the scan of the visual field corresponding to a next scanning point (a scanning point R15) by displaying the static visual target to scan the visual field corresponding to the next scanning point (the scanning point R15), at the next scanning point (i.e., the scanning point R15), immediately after stopping displaying, promptly when detecting the response via the first input device (for example, the right cursor key 303A in an embodiment of the present invention) through the first detection means (in this case, the response made by the subject of the static visual target displayed at the scanning point R14 being perceivable in the visual field), the displayed static visual target (the static visual target displayed at the scanning point R14). (Forming a part of visual target displaying and controlling means.)
(An immediate post first detection scan continuation means.)

The CPU 501 displays now, for example, a static visual target at a scanning point R15 in accordance with the program for realizing the present invention of a static visual field scanning apparatus. (Forming a part of visual target displaying and controlling means.)

And then the CPU 501, while displaying the static visual target at the scanning point R15, waits for a response during the period in which the response via the first input device (for example, the right cursor key 303A in an embodiment of the present invention) is not detected by the first detection means and the response via the second input device (for example, the left cursor key 303B in an embodiment of the present invention) is not detected by the second detection means, in accordance with the program for realizing the present invention of a static visual field scanning apparatus. (A response waiting means.)

Suppose now that the subject who fixates the fixation image 2 can visually perceive the static visual target displayed at the scanning point R15 as well.

The subject makes, at the time when the subject was able to visually perceive in the visual field the static visual target displayed at the scanning point R15, the response of the static visual target being perceivable (for example, the momentary depression of the right cursor key 303A in an embodiment of the present invention), via the first input device (for example, the right cursor key 303A in an embodiment of the present invention).

The CPU 501 continues the scan of the visual field corresponding to a next scanning point (a scanning point R16) by displaying the static visual target to scan the visual field corresponding to the next scanning point (the scanning point R16), at the next scanning point (i.e., the scanning point R16), immediately after stopping displaying, promptly when detecting the response via the first input device (for example, the right cursor key 303A in an embodiment of the present invention) through the first detection means (in this case, the response made by the subject of the static visual target displayed at the scanning point R15 being perceivable in the visual field), the displayed static visual target (the static visual target displayed at the scanning point R15). (Forming a part of visual target displaying and controlling means.)

(An immediate post first detection scan continuation means.)

The CPU 501 displays now, for example, a static visual target at a scanning point R16 in accordance with the program for realizing the present invention of a static visual field scanning apparatus. (Forming a part of visual target displaying and controlling means.)

And then the CPU 501, while displaying the static visual target at the scanning point R16, waits for a response during the period in which the response via the first input device (for example, the right cursor key 303A in an embodiment of the present invention) is not detected by the first detection means and the response via the second input device (for example, the left cursor key 303B in an embodiment of the present invention) is not detected by the second detection means, in accordance with the program for realizing the present invention of a static visual field scanning apparatus. (A response waiting means.)

Suppose now that the subject who fixates the fixation image 2 cannot visually perceive the static visual target displayed at the scanning point R16.

When the subject cannot perceive in the visual field the static visual target displayed at the scanning point R16, the subject can instantaneously make a response of the static visual target (the static visual target displayed at the scanning point R16) being unperceivable (for example, the momentary depression of the left cursor key 303B in an embodiment of the present invention), via the second input device (for example, the left cursor key 303B in an embodiment of the present invention).

The CPU 501 continues the scan of the visual field corresponding to a next scanning point (a scanning point R17) by displaying the static visual target to scan the visual field corresponding to the next scanning point (the scanning point R17), at the next scanning point (i.e., the scanning point R17), immediately after stopping displaying, promptly when detecting the response via the second input device (for example, the left cursor key 303B in an embodiment of the present invention) through the second detection means (in this case, the response made by the subject of the static visual target displayed at the scanning point R16 being unperceivable in the visual field), the displayed static visual target (the static visual target displayed at the scanning point R16). (Forming a part of visual target displaying and controlling means.)

(An immediate post second detection scan continuation means.)

The CPU 501 stores in a memory device (for example, such as a RAM 502, a HDD 504, etc.) the coordinates of the static visual target displayed, either at the time of the response via the first input device (for example, the right cursor key 303A in an embodiment of the present invention) (for example, the momentary depression of the right cursor key 303A in an embodiment of the present invention) being detected through the first detection means or at the time of the response via the second input device (for example, the left cursor key 303B in an embodiment of the present invention) (for example, the momentary depression of the left cursor key 303B in an embodiment of the present invention) being detected through the second detection means, in the visual field scanning screen 1 by the CPU 501 (Forming a part of visual target display coordinates storing means), and when the response via the second input device (for example, the left cursor key 303B in an embodiment of the present invention) (for example, the momentary depression of the left cursor key 303B in an embodiment of the present invention) is detected by the second detection means, the CPU 501 records, in reference to the coordinates stored in the memory device (for example, such as the RAM 502, the HDD 504, etc.) at the time of the detection (in this instance, the coordinates of the scanning point R16), at a position of a visual field mapping screen 3 (the CPU 501 generates the visual field mapping screen 3 on an output device (for example, the display 304, etc.). (the visual field mapping screen 3 may be generated on the output device when the CPU 501 generates the visual field scanning screen 1 on the output device.) (A visual field mapping screen generating means.)) which corresponds to the coordinates (in this instance, the coordinates of the scanning point R16), a symbol (in this instance, a visual target perception inability symbol f16) which represents the inability to visually perceive the static visual target displayed at the coordinates (in this instance, the coordinates of the scanning point R16) by the CPU 501. (A visual target perception inability symbol mapping means.)

(In this instance, the next scanning point (the scanning point R17) is determined by a second completion judgement means and a post second completion judgement the next scanning point calculation means.)

(That is, the CPU 501, after detecting the response via the second input device (for example, the left cursor key 303B in an embodiment of the present invention) through the second detection means (in this case, the response made by the subject of the static visual target displayed at the scanning point R16 being unperceivable in the visual field), makes a judgement, using the arithmetic unit, about whether the scan of the scanning points along the scan line (i.e., the scan line R1) which the static visual target displayed in the visual field scanning screen 1 at the time of the detection (the static visual target displayed at the scanning point R16), belonged to and lay at has been completed or not (whether the scan along the scan line R1 has been completed up to the scanning point R1$n$ or not).

(A second completion judgement means.)

(In this instance, the CPU 501 makes a judgement that the scan of the scanning points on the scan line (the scan line R1) (the scan up to the scanning point R1$n$) is uncompleted, and designates through the calculation of the arithmetic unit as the next scanning point the scanning point (the scanning point R17) that shares the scan line (the scan line R1) with, and is adjacent to, the static visual target displayed at the time of the response via the second input device (for example, the left cursor key 303B in an embodiment of the present invention) being detected through the second detection means (the static visual target displayed at the scanning point R16).) (A post second completion judgement the next scanning point calculation means.)

(In an embodiment of the present invention of a static visual field scanning apparatus, even, for example, if the subject were holding down the left cursor key 303B, the scanning point as the next scanning point will not move from the scanning point R17 to the scanning point R18 and to the scanning point R19, . . . , etc., for example. The scanning point operates to move only once to one depression of the left cursor key 303B.)

The CPU 501 displays now, for example, a static visual target at a scanning point R17 in accordance with the program for realizing the present invention of a static visual field scanning apparatus. (Forming a part of visual target displaying and controlling means.)

And then the CPU 501, while displaying the static visual target at the scanning point R17, waits for a response during the period in which the response via the first input device (for example, the right cursor key 303A in an embodiment of the present invention) is not detected by the first detection means and the response via the second input device (for example, the left cursor key 303B in an embodiment of the present invention) is not detected by the second detection means, in accordance with the program for realizing the present invention of a static visual field scanning apparatus. (A response waiting means.)

Suppose now that the subject who fixates the fixation image 2 cannot visually perceive the static visual target displayed at the scanning point R17 as well.

When the subject cannot perceive in the visual field the static visual target displayed at the scanning point R17, the subject can instantaneously make a response of the static visual target (the static visual target displayed at the scanning point R17) being unperceivable (for example, the momentary depression of the left cursor key 303B in an embodiment of the present invention), via the second input device (for example, the left cursor key 303B in an embodiment of the present invention).

The CPU 501 continues the scan of the visual field corresponding to a next scanning point (a scanning point R18) by displaying the static visual target to scan the visual field corresponding to the next scanning point (the scanning point R18), at the next scanning point (i.e., the scanning point R18), immediately after stopping displaying, promptly when detecting the response via the second input device (for example, the left cursor key 303B in an embodiment of the present invention) through the second detection means (in this case, the response made by the subject of the static visual target displayed at the scanning point R17 being unperceivable in the visual field), the displayed static visual target (the static visual target displayed at the scanning point R17). (Forming a part of visual target displaying and controlling means.)
(An immediate post second detection scan continuation means.)

The CPU 501 stores in the memory device (for example, such as the RAM 502, the HDD 504, etc.) the coordinates of the static visual target displayed, either at the time of the response via the first input device (for example, the right cursor key 303A in an embodiment of the present invention) (for example, the momentary depression of the right cursor key 303A in an embodiment of the present invention) being detected through the first detection means or at the time of the response via the second input device (for example, the left cursor key 303B in an embodiment of the present invention) (for example, the momentary depression of the left cursor key 303B in an embodiment of the present invention) being detected through the second detection means, in the visual field scanning screen 1 by the CPU 501 (Forming a part of visual target display coordinates storing means),
and when the response via the second input device (for example, the left cursor key 303B in an embodiment of the present invention) (for example, the momentary depression of the left cursor key 303B in an embodiment of the present invention) is detected by the second detection means, the CPU 501 records, in reference to the coordinates stored in the memory device (for example, such as the RAM 502, the HDD 504, etc.) at the time of the detection (in this instance, the coordinates of the scanning point R17), at a position of a visual field mapping screen 3 (the CPU 501 generates the visual field mapping screen 3 on an output device (for example, the display 304, etc.). (the visual field mapping screen 3 may be generated on the output device when the CPU 501 generates the visual field scanning screen 1 on the output device.) (A visual field mapping screen generating means.)) which corresponds to the coordinates (in this instance, the coordinates of the scanning point R17), a symbol (in this instance, a visual target perception inability symbol f17) which represents the inability to visually perceive the static visual target displayed at the coordinates (in this instance, the coordinates of the scanning point R17) by the CPU 501. (A visual target perception inability symbol mapping means.)

(In this instance, the next scanning point (the scanning point R18) is determined by the second completion judgement means and the post second completion judgement the next scanning point calculation means.
(Like the case where the scanning point R17 was determined as a next scanning point, as mentioned above.))

The CPU 501 displays now, for example, a static visual target at a scanning point R18 in accordance with the program for realizing the present invention of a static visual field scanning apparatus. (Forming a part of visual target displaying and controlling means.)

And then the CPU 501, while displaying the static visual target at the scanning point R18, waits for a response during the period in which the response via the first input device (for example, the right cursor key 303A in an embodiment of the present invention) is not detected by the first detection means and the response via the second input device (for example, the left cursor key 303B in an embodiment of the present invention) is not detected by the second detection means, in accordance with the program for realizing the present invention of a static visual field scanning apparatus. (A response waiting means.)

Suppose now that the subject who fixates the fixation image 2 cannot visually perceive the static visual target displayed at the scanning point R18 as well.

When the subject cannot perceive in the visual field the static visual target displayed at the scanning point R18, the subject can instantaneously make a response of the static visual target (the static visual target displayed at the scanning point R18) being unperceivable (for example, the momentary depression of the left cursor key 303B in an embodiment of the present invention), via the second input device (for example, the left cursor key 303B in an embodiment of the present invention).

The CPU 501 continues the scan of the visual field corresponding to a next scanning point (a scanning point R19) by displaying the static visual target to scan the visual field corresponding to the next scanning point (the scanning point R19), at the next scanning point (i.e., the scanning point R19), immediately after stopping displaying, promptly when detecting the response via the second input device (for example, the left cursor key 303B in an embodiment of the present invention) through the second detection means (in this case, the response made by the subject of the static visual target displayed at the scanning point R18 being unperceivable in the visual field), the displayed static visual target (the static visual target displayed at the scanning point R18). (Forming a part of visual target displaying and controlling means.)
(An immediate post second detection scan continuation means.)

The CPU 501 stores in the memory device (for example, such as the RAM 502, the HDD 504, etc.) the coordinates of the static visual target displayed, either at the time of the response via the first input device (for example, the right cursor key 303A in an embodiment of the present invention) (for example, the momentary depression of the right cursor key 303A in an embodiment of the present invention) being detected through the first detection means or at the time of the response via the second input device (for example, the left cursor key 303B in an embodiment of the present invention) (for example, the momentary depression of the left cursor key 303B in an embodiment of the present invention) being detected through the second detection means, in the visual field scanning screen 1 by the CPU 501 (Forming a part of visual target display coordinates storing means), and when the response via the second input device (for example, the left cursor key 303B in an embodiment of the present invention) (for example, the momentary depression of the left cursor key 303B in an embodiment of the present invention) is detected by the second detection means, the CPU 501 records, in reference to the coordinates stored in the memory device (for example, such as the RAM 502, the HDD 504, etc.) at the time of the detection (in this instance, the coordinates of the scanning point R18), at a position of a visual field mapping screen 3 which corresponds to the coordinates (in this instance, the coordinates of the scanning point R18), a symbol (in this instance, a visual target perception inability symbol f18) which represents the inability to visually perceive the static visual target displayed at the coordinates (in this instance, the coordinates of the scanning point R18) by the CPU 501. (A visual target perception inability symbol mapping means.)

(In this instance, the next scanning point (the scanning point R19) is determined by the second completion judgement means and the post second completion judgement the next scanning point calculation means.)

After the similar processing, the CPU 501 displays now a static visual target at a scanning point R110, for example. (Forming a part of visual target displaying and controlling means.)

And then the CPU 501, while displaying the static visual target at the scanning point R110, waits for a response during the period in which the response via the first input device (for example, the right cursor key 303A in an embodiment of the present invention) is not detected by the first detection means and the response via the second input device (for example, the left cursor key 303B in an embodiment of the present invention) is not detected by the second detection means, in accordance with the program for realizing the present invention of a static visual field scanning apparatus. (A response waiting means.)

Suppose now that the subject who fixates the fixation image 2 cannot visually perceive the static visual target displayed at the scanning point R110 as well.

When the subject cannot perceive in the visual field the static visual target displayed at the scanning point R110, the subject can instantaneously make a response of the static visual target (the static visual target displayed at the scanning point R110) being unperceivable (for example, the momentary depression of the left cursor key 303B in an embodiment of the present invention), via the second input device (for example, the left cursor key 303B in an embodiment of the present invention).

The CPU 501 continues the scan of the visual field corresponding to a next scanning point (a scanning point R111) by displaying the static visual target to scan the visual field corresponding to the next scanning point (the scanning point R111), at the next scanning point (i.e., the scanning point R111), immediately after stopping displaying, promptly when detecting the response via the second input device (for example, the left cursor key 303B in an embodiment of the present invention) through the second detection means (in this case, the response made by the subject of the static visual target displayed at the scanning point R110 being unperceivable in the visual field), the displayed static visual target (the static visual target displayed at the scanning point R110). (Forming a part of visual target displaying and controlling means.)

(An immediate post second detection scan continuation means.)

The CPU 501 stores in the memory device (for example, such as the RAM 502, the HDD 504, etc.) the coordinates of the static visual target displayed, either at the time of the response via the first input device (for example, the right cursor key 303A in an embodiment of the present invention) (for example, the momentary depression of the right cursor key 303A in an embodiment of the present invention) being detected through the first detection means or at the time of the response via the second input device (for example, the left cursor key 303B in an embodiment of the present invention) (for example, the momentary depression of the left cursor key 303B in an embodiment of the present invention) being detected through the second detection means, in the visual field scanning screen 1 by the CPU 501 (Forming a part of visual target display coordinates storing means), and when the response via the second input device (for example, the left cursor key 303B in an embodiment of the present invention) (for example, the momentary depression of the left cursor key 303B in an embodiment of the present invention) is detected by the second detection means, the CPU 501 records, in reference to the coordinates stored in the memory device (for example, such as the RAM 502, the HDD 504, etc.) at the time of the detection (in this instance, the coordinates of the scanning point R110), at a position of a visual field mapping screen 3 which corresponds to the coordinates (in this instance, the coordinates of the scanning point R110), a symbol (in this instance, a visual target perception inability symbol f110) which represents the inability to visually perceive the static visual target displayed at the coordinates (in this instance, the coordinates of the scanning point R110) by the CPU 501. (A visual target perception inability symbol mapping means.)

(In this instance, the next scanning point (the scanning point R111) is determined by the second completion judgement means and the post second completion judgement the next scanning point calculation means.)

The CPU 501 displays now, for example, a static visual target at a scanning point R111 in accordance with the program for realizing the present invention of a static visual field scanning apparatus. (Forming a part of visual target displaying and controlling means.)

And then the CPU 501, while displaying the static visual target at the scanning point R111, waits for a response during the period in which the response via the first input device (for example, the right cursor key 303A in an embodiment of the present invention) is not detected by the first detection means and the response via the second input device (for example, the left cursor key 303B in an embodiment of the present invention) is not detected by the second detection means, in accordance with the program for realizing the present invention of a static visual field scanning apparatus. (A response waiting means.)

Suppose now that the subject who fixates the fixation image 2 can visually perceive the static visual target displayed at the scanning point R111.

The subject makes, at the time when the subject was able to visually perceive in the visual field the static visual target displayed at the scanning point R111, the response of the static visual target being perceivable (for example, the momentary depression of the right cursor key 303A in an embodiment of the present invention), via the first input device (for example, the right cursor key 303A in an embodiment of the present invention).

The CPU 501 continues the scan of the visual field corresponding to a next scanning point (a scanning point R112) by displaying the static visual target to scan the visual field corresponding to the next scanning point (the scanning point R112), at the next scanning point (i.e., the scanning point R112), immediately after stopping displaying, promptly when detecting the response via the first input device (for example, the right cursor key 303A in an embodiment of the present invention) through the first detection means (in this case, the response made by the subject of the static visual target displayed at the scanning point R111 being perceivable in the visual field), the displayed static visual target (the static visual target displayed at the scanning point R111). (Forming a part of visual target displaying and controlling means.)

(An immediate post first detection scan continuation means.)

The CPU 501 displays now, for example, a static visual target at a scanning point R112 in accordance with the program for realizing the present invention of a static visual field scanning apparatus. (Forming a part of visual target displaying and controlling means.)

And then the CPU 501, while displaying the static visual target at the scanning point R112, waits for a response during the period in which the response via the first input device (for example, the right cursor key 303A in an embodiment of the present invention) is not detected by the first detection means and the response via the second input device (for example, the left cursor key 303B in an embodiment of the present invention) is not detected by the second detection means, in accordance with the program for realizing the present invention of a static visual field scanning apparatus. (A response waiting means.)

Suppose now that the subject who fixates the fixation image 2 can visually perceive the static visual target displayed at the scanning point R112 as well.

The subject makes, at the time when the subject was able to visually perceive in the visual field the static visual target displayed at the scanning point R112, the response of the static visual target being perceivable (for example, the momentary depression of the right cursor key 303A in an embodiment of the present invention), via the first input device (for example, the right cursor key 303A in an embodiment of the present invention).

The CPU 501 continues the scan of the visual field corresponding to a next scanning point (a scanning point R113) by displaying the static visual target to scan the visual field corresponding to the next scanning point (the scanning point R113), at the next scanning point (i.e., the scanning point R113), immediately after stopping displaying, promptly when detecting the response via the first input device (for example, the right cursor key 303A in an embodiment of the present invention) through the first detection means (in this case, the response made by the subject of the static visual target displayed at the scanning point R112 being perceivable in the visual field), the displayed static visual target (the static visual target displayed at the scanning point R112). (Forming a part of visual target displaying and controlling means.)

(An immediate post first detection scan continuation means.)

After the similar processing, the CPU 501 displays now a static visual target at a scanning point R1($n$−1), for example. (Forming a part of visual target displaying and controlling means.)

And then the CPU 501, while displaying the static visual target at the scanning point R1($n$−1), waits for a response during the period in which the response via the first input device (for example, the right cursor key 303A in an embodiment of the present invention) is not detected by the first detection means and the response via the second input device (for example, the left cursor key 303B in an embodiment of the present invention) is not detected by the second detection means, in accordance with the program for realizing the present invention of a static visual field scanning apparatus. (A response waiting means.)

Suppose now that the subject who fixates the fixation image 2 cannot visually perceive the static visual target displayed at the scanning point R1($n$−1).

When the subject cannot perceive in the visual field the static visual target displayed at the scanning point R1($n$−1), the subject can instantaneously make a response of the static visual target (the static visual target displayed at the scanning point R1($n$−1)) being unperceivable (for example, the momentary depression of the left cursor key 303B in an embodiment of the present invention), via the second input device (for example, the left cursor key 303B in an embodiment of the present invention).

The CPU 501 continues the scan of the visual field corresponding to a next scanning point (a scanning point R1$n$) by displaying the static visual target to scan the visual field corresponding to the next scanning point (the scanning point R1$n$), at the next scanning point (i.e., the scanning point R1$n$), immediately after stopping displaying, promptly when detecting the response via the second input device (for example, the left cursor key 303B in an embodiment of the present invention) through the second detection means (in this case, the response made by the subject of the static visual target displayed at the scanning point R1($n$−1) being unperceivable in the visual field), the displayed static visual target (the static visual target displayed at the scanning point R1($n$−1)). (Forming a part of visual target displaying and controlling means.)

(An immediate post second detection scan continuation means.)

The CPU 501 stores in the memory device (for example, such as the RAM 502, the HDD 504, etc.) the coordinates of the static visual target displayed, either at the time of the response via the first input device (for example, the right cursor key 303A in an embodiment of the present invention) (for example, the momentary depression of the right cursor key 303A in an embodiment of the present invention) being detected through the first detection means or at the time of the response via the second input device (for example, the left cursor key 303B in an embodiment of the present invention) (for example, the momentary depression of the left cursor key 303B in an embodiment of the present invention) being detected through the second detection means, in the visual field scanning screen 1 by the CPU 501 (Forming a part of visual target display coordinates storing means), and when the response via the second input device (for example, the left cursor key 303B in an embodiment of the present invention) (for example, the momentary depression of the left cursor key 303B in an embodiment of the present invention) is detected by the second detection means, the CPU 501 records, in reference to the coordinates stored in the memory device (for example, such as the RAM 502, the HDD 504, etc.) at the time of the detection (in this instance, the coordinates of the scanning point R1($n$−1)), at a position of a visual field mapping screen 3 which corresponds to the coordinates (in this instance, the coordinates of the scanning point R1($n$−1)), a symbol (in this instance, a visual target perception inability symbol f1($n$−1)) which represents the inability to visually perceive the static visual target displayed at the coordinates (in this instance, the coordinates of the scanning point R1($n$−1)) by the CPU 501. (A visual target perception inability symbol mapping means.)

(In this instance, the next scanning point (the scanning point R1$n$) is determined by the second completion judgement means and the post second completion judgement the next scanning point calculation means.)

The CPU 501 displays now, for example, a static visual target at a scanning point R1*n* in accordance with the program for realizing the present invention of a static visual field scanning apparatus. (Forming a part of visual target displaying and controlling means.)

And then the CPU 501, while displaying the static visual target at the scanning point R1*n*, waits for a response during the period in which the response via the first input device (for example, the right cursor key 303A in an embodiment of the present invention) is not detected by the first detection means and the response via the second input device (for example, the left cursor key 303B in an embodiment of the present invention) is not detected by the second detection means, in accordance with the program for realizing the present invention of a static visual field scanning apparatus. (A response waiting means.)

Suppose now that the subject who fixates the fixation image 2 cannot visually perceive the static visual target displayed at the scanning point R1*n*.

When the subject cannot perceive in the visual field the static visual target displayed at the scanning point R1*n*, the subject can instantaneously make a response of the static visual target (the static visual target displayed at the scanning point R1*n*) being unperceivable (for example, the momentary depression of the left cursor key 303B in an embodiment of the present invention), via the second input device (for example, the left cursor key 303B in an embodiment of the present invention).

The CPU 501 continues the scan of the visual field corresponding to a next scanning point (a scanning point R21) by displaying the static visual target to scan the visual field corresponding to the next scanning point (the scanning point R21), at the next scanning point (i.e., the scanning point R21), immediately after stopping displaying, promptly when detecting the response via the second input device (for example, the left cursor key 303B in an embodiment of the present invention) through the second detection means (in this case, the response made by the subject of the static visual target displayed at the scanning point R1*n* being unperceivable in the visual field), the displayed static visual target (the static visual target displayed at the scanning point R1*n*). (Forming a part of visual target displaying and controlling means.)

(An immediate post second detection scan continuation means.)

(In the scanning aspect of an embodiment of the present invention of a static visual field scanning apparatus, the scanning by the static visual target begins at the location of the scanning point R11 and advances from the scanning point R11, rightward along the scan line R1, to the scanning point R11, to the scanning point R12, . . . , and to the scanning point R1*n*, and after completing the scan of the scanning point R1*n* in a right edge of the scanning region 1A, the scan line is switched to the scan line R2 which is located inferior to, and adjacent to, the scan line R1, and the similar scanning is conducted rightward along the scan line R2 from the scanning point R21 of a left edge of the scanning region 1A, and by iterating the similar switching of the scan line and the similar scanning along the scan line, the scanning is conducted up to the scanning point Rmn of a lower right corner of the scanning region 1A, but the scanning aspect using the static visual target may be set otherwise, with each scan line alternating its directionality of scanning, such as a rightward scanning on the scan line R1, a leftward scanning on the scan line R2, a rightward scanning on the scan line R3, etc.)

The CPU 501 stores in the memory device (for example, such as the RAM 502, the HDD 504, etc.) the coordinates of the static visual target displayed, either at the time of the response via the first input device (for example, the right cursor key 303A in an embodiment of the present invention) (for example, the momentary depression of the right cursor key 303A in an embodiment of the present invention) being detected through the first detection means or at the time of the response via the second input device (for example, the left cursor key 303B in an embodiment of the present invention) (for example, the momentary depression of the left cursor key 303B in an embodiment of the present invention) being detected through the second detection means, in the visual field scanning screen 1 by the CPU 501 (Forming a part of visual target display coordinates storing means), and when the response via the second input device (for example, the left cursor key 303B in an embodiment of the present invention) (for example, the momentary depression of the left cursor key 303B in an embodiment of the present invention) is detected by the second detection means, the CPU 501 records, in reference to the coordinates stored in the memory device (for example, such as the RAM 502, the HDD 504, etc.) at the time of the detection (in this instance, the coordinates of the scanning point R1*n*), at a position of a visual field mapping screen 3 which corresponds to the coordinates (in this instance, the coordinates of the scanning point R1*n*), a symbol (in this instance, a visual target perception inability symbol f1*n*) which represents the inability to visually perceive the static visual target displayed at the coordinates (in this instance, the coordinates of the scanning point R1*n*) by the CPU 501. (A visual target perception inability symbol mapping means.)

(In this instance, the next scanning point (the scanning point R21) is determined by the second completion judgement means and the post second completion judgement the next scanning point calculation means.) (That is, the CPU 501, after detecting the response via the second input device (for example, the left cursor key 303B in an embodiment of the present invention) through the second detection means (in this case, the response made by the subject of the static visual target displayed at the scanning point R1*n* being unperceivable in the visual field), makes a judgement, using the arithmetic unit, about whether the scan of the scanning points along the scan line (i.e., the scan line R1) which the static visual target displayed in the visual field scanning screen 1 at the time of the detection (the static visual target displayed at the scanning point R1*n*), belonged to and lay at has been completed or not (whether the scan along the scan line R1 has been completed up to the scanning point R1*n* or not).

(A second completion judgement means.)

(In this instance, the CPU 501 makes a judgement through the calculation of the arithmetic unit that the scan of the scanning points on the scan line (the scan line R1) (the scan up to the scanning point R1*n*) is completed, and switches the scan line for scanning to the scan line (the scan line R2, in an embodiment of the present invention) adjacent to the scan line (the scan line R1) which the static visual target, displayed by the CPU 501 at the time of the response (for example, the momentary depression of the left cursor key 303B in an embodiment of the present invention), via the second input device (for example, the left cursor key 303B in an embodiment of the present invention), being detected through the second detection means, belonged to and lay at, and designates as the next scanning point the scanning point (set, in an embodiment of the present invention, at the scanning point R21 located in a left edge of the scan line R2) that lies in an edge of the scan line (the scan line R2 in an embodiment of the present invention).

(A post second completion judgement the next scanning point calculation means.)

(In an embodiment of the present invention of a static visual field scanning apparatus, even, for example, if the subject were holding down the left cursor key 303B, the scanning point as the next scanning point will not move from the scanning point R21 to the scanning point R22, ..., etc., for example. The scanning point operates to move only once to one depression of the left cursor key 303B.)

The CPU 501 displays now, for example, a static visual target at a scanning point R21 in accordance with the program for realizing the present invention of a static visual field scanning apparatus. (Forming a part of visual target displaying and controlling means.)

And then the CPU 501, while displaying the static visual target at the scanning point R21, waits for a response during the period in which the response via the first input device (for example, the right cursor key 303A in an embodiment of the present invention) is not detected by the first detection means and the response via the second input device (for example, the left cursor key 303B in an embodiment of the present invention) is not detected by the second detection means, in accordance with the program for realizing the present invention of a static visual field scanning apparatus. (A response waiting means.)

Suppose now that the subject who fixates the fixation image 2 cannot visually perceive the static visual target displayed at the scanning point R21.

When the subject cannot perceive in the visual field the static visual target displayed at the scanning point R21, the subject can instantaneously make a response of the static visual target (the static visual target displayed at the scanning point R21) being unperceivable (for example, the momentary depression of the left cursor key 303B in an embodiment of the present invention), via the second input device (for example, the left cursor key 303B in an embodiment of the present invention).

The CPU 501 continues the scan of the visual field corresponding to a next scanning point (a scanning point R22) by displaying the static visual target to scan the visual field corresponding to the next scanning point (the scanning point R22), at the next scanning point (i.e., the scanning point R22), immediately after stopping displaying, promptly when detecting the response via the second input device (for example, the left cursor key 303B in an embodiment of the present invention) through the second detection means (in this case, the response made by the subject of the static visual target displayed at the scanning point R21 being unperceivable in the visual field), the displayed static visual target (the static visual target displayed at the scanning point R21). (Forming a part of visual target displaying and controlling means.)

(An immediate post second detection scan continuation means.)

The CPU 501 stores in the memory device (for example, such as the RAM 502, the HDD 504, etc.) the coordinates of the static visual target displayed, either at the time of the response via the first input device (for example, the right cursor key 303A in an embodiment of the present invention) (for example, the momentary depression of the right cursor key 303A in an embodiment of the present invention) being detected through the first detection means or at the time of the response via the second input device (for example, the left cursor key 303B in an embodiment of the present invention) (for example, the momentary depression of the left cursor key 303B in an embodiment of the present invention) being detected through the second detection means, in the visual field scanning screen 1 by the CPU 501 (Forming a part of visual target display coordinates storing means), and when the response via the second input device (for example, the left cursor key 303B in an embodiment of the present invention) (for example, the momentary depression of the left cursor key 303B in an embodiment of the present invention) is detected by the second detection means, the CPU 501 records, in reference to the coordinates stored in the memory device (for example, such as the RAM 502, the HDD 504, etc.) at the time of the detection (in this instance, the coordinates of the scanning point R21), at a position of a visual field mapping screen 3 which corresponds to the coordinates (in this instance, the coordinates of the scanning point R21), a symbol (in this instance, a visual target perception inability symbol f21) which represents the inability to visually perceive the static visual target displayed at the coordinates (in this instance, the coordinates of the scanning point R21) by the CPU 501. (A visual target perception inability symbol mapping means.)

(In this instance, the next scanning point (the scanning point R22) is determined by the second completion judgement means and the post second completion judgement the next scanning point calculation means.) (That is, the CPU 501, after detecting the response via the second input device (for example, the left cursor key 303B in an embodiment of the present invention) through the second detection means (in this case, the response made by the subject of the static visual target displayed at the scanning point R21 being unperceivable in the visual field), makes a judgement, using the arithmetic unit, about whether the scan of the scanning points along the scan line (i.e., the scan line R2) which the static visual target displayed in the visual field scanning screen 1 at the time of the detection (the static visual target displayed at the scanning point R21), belonged to and lay at has been completed or not (whether the scan along the scan line R2 has been completed up to the scanning point of a right edge or not). (A second completion judgement means.)

(In this instance, the CPU 501 makes a judgement that the scan of the scanning points on the scan line (the scan line R2) (the scan along the scan line R2 up to the scanning point of a right edge (of the scanning region 1A)) is uncompleted, and designates through the calculation of the arithmetic unit as the next scanning point the scanning point (the scanning point R22) that shares the scan line (the scan line R2) with, and is adjacent to, the static visual target displayed at the time of the response via the second input device (for example, the left cursor key 303B in an embodiment of the present invention) being detected through the second detection means (the static visual target displayed at the scanning point R21).) (A post second completion judgement the next scanning point calculation means.)

After the similar processing, the CPU 501 displays now a static visual target at a scanning point Rm(n−1), for example. (Forming a part of visual target displaying and controlling means.)

And then the CPU 501, while displaying the static visual target at the scanning point Rm(n−1), waits for a response during the period in which the response via the first input device (for example, the right cursor key 303A in an embodiment of the present invention) is not detected by the first detection means and the response via the second input device (for example, the left cursor key 303B in an embodiment of the present invention) is not detected by the second detection means, in accordance with the program for realizing the present invention of a static visual field scanning apparatus. (A response waiting means.)

Suppose now that the subject who fixates the fixation image 2 can visually perceive the static visual target displayed at the scanning point Rm(n−1).

The subject makes, at the time when the subject was able to visually perceive in the visual field the static visual target displayed at the scanning point Rm(n−1), the response of the static visual target being perceivable (for example, the momentary depression of the right cursor key 303A in an embodiment of the present invention), via the first input device (for example, the right cursor key 303A in an embodiment of the present invention).

The CPU 501 continues the scan of the visual field corresponding to a next scanning point (a scanning point Rmn) by displaying the static visual target to scan the visual field corresponding to the next scanning point (the scanning point Rmn), at the next scanning point (i.e., the scanning point Rmn), immediately after stopping displaying, promptly when detecting the response via the first input device (for example, the right cursor key 303A in an embodiment of the present invention) through the first detection means (in this case, the response made by the subject of the static visual target displayed at the scanning point Rm(n−1) being perceivable in the visual field), the displayed static visual target (the static visual target displayed at the scanning point Rm(n−1)). (Forming a part of visual target displaying and controlling means.)
(An immediate post first detection scan continuation means.)
(In this instance, the next scanning point (the scanning point Rmn) is determined by the first completion judgement means and the post first completion judgement the next scanning point calculation means.)
(That is, the CPU 501, after detecting the response via the first input device (for example, the right cursor key 303A in an embodiment of the present invention) through the first detection means (in this case, the response made by the subject of the static visual target displayed at the scanning point Rm(n−1) being perceivable in the visual field), makes a judgement, using an arithmetic unit, about whether the scan of the scanning points along the scan line (i.e., the scan line Rm) which the static visual target displayed in the visual field scanning screen 1 at the time of the detection (the static visual target displayed at the scanning point Rm(n−1)), belonged to and lay at has been completed or not (whether the scan along the scan line Rm has been completed up to the scanning point Rmn or not). (A first completion judgement means.)

(In this instance, the CPU 501 makes a judgement that the scan of the scanning points on the scan line (the scan line Rm) (the scan up to the scanning point Rmn) is uncompleted, and designates through the calculation of the arithmetic unit as the next scanning point the scanning point (the scanning point Rmn) that shares the scan line (the scan line Rm) with, and is adjacent to, the static visual target displayed at the time of the response via the first input device (for example, the right cursor key 303A in an embodiment of the present invention) being detected through the first detection means (the static visual target displayed at the scanning point Rm(n−1)).) (A post first completion judgement the next scanning point calculation means.)

The CPU 501 displays now, for example, a static visual target at a scanning point Rmn in accordance with the program for realizing the present invention of a static visual field scanning apparatus. (Forming a part of visual target displaying and controlling means.)

When the scan of the scanning point Rmn is completed by the similar processing, the scanning of the visual field scanning screen 1 comes to completion. (The scanning end point is not necessarily limited to the scanning point Rmn.).

Regarding a static visual field scanning and visual field mapping process carried out by the CPU 501 in accordance with a program for realizing the present invention of a static visual field scanning apparatus, the detailed explanation will be disclosed as below while referring to FIG. 4A, FIG. 4B, FIG. 5A, FIG. 5B, and FIG. 6, and FIG. 2 and FIG. 9.

FIG. 4A, FIG. 4B, FIG. 5A, FIG. 5B, and FIG. 6 are flow charts showing a static visual field scanning and visual field mapping process in a static visual field scanning apparatus to be carried out by a computer shown in FIG. 7.

FIG. 2 shows an embodiment of the scanning, operation, and static visual field mapping aspect of the present invention of a static visual field scanning apparatus.

FIG. 9 shows a preferred embodiment of the display screen of the present invention of a static visual field scanning apparatus.

(Hereinafter, in the explanation of coordinates in an embodiment of the present invention, positions are described assuming that an x coordinate axis shall be generated rightward from the origin and a y coordinate axis shall be generated downward from the origin.)

At the step of S2 in a static visual field scanning and visual field mapping process, a CPU 501 generates an ID2 window for a visual field scanning screen 1, on an output device (for example, a display 304).
(In an embodiment of the present invention, the CPU 501 sets, for example, the width of 660+150 dots in the x direction and the height of 546−10 dots in the y direction for the visual field scanning screen1.)

At the step of S3, the x coordinate of the upper left corner of a scanning region 1A, measured relative to a visual field scanning screen origin 5, is substituted into a variable stcounxv by the CPU 501.

At the step of S3, the y coordinate of the upper left corner of the scanning region 1A, measured relative to the visual field scanning screen origin 5, is substituted into a variable stcounyv by the CPU 501.

The scanning region 1A is a region where at least one scan line Ri (i=1 through m) is set, in the visual field scanning screen 1, by a scan line setting means.
(A scanning region 1A may be set over the visual field scanning screen 1.)

At the step of S4, the x coordinate of the lower right corner of the scanning region 1A, measured relative to the visual field scanning screen origin 5, is substituted into a variable edx by the CPU 501.

At the step of S4, the y coordinate of the lower right corner of the scanning region 1A, measured relative to the visual field scanning screen origin 5, is substituted into a variable edy by the CPU 501.

The scanning region 1A is a region where at least one scan line Ri (i=1 through m) is set, in the visual field scanning screen 1, by a scan line setting means.
(A scanning region 1A may be set over the visual field scanning screen 1.)

At the step of S5, the CPU 501 initializes the value of a variable counx to be 0.
(The value of the variable counx is associated with the value of j for a scanning point Rij (i=1 through m, j=1 through n). In an embodiment of the present invention, the value of counx+1 specifies the value of j. At the step of S5, initializing the value of the variable counx to be 0, the CPU 501 sets an initial scanning point (i.e., a scanning start point) at the first scanning point, for example, from the left on a scan line Ri (i=1 through m).)

At the step of S5, the CPU 501 initializes the value of a variable couny to be 0.

(The value of the variable couny is associated with the value of i for a scan line Ri (i=1 through m). In an embodiment of the present invention, the value of couny+1 specifies the value of i. At the step of S5, initializing the value of the variable couny to be 0, the CPU 501 sets an initial scan line (i.e., a starting scan line) to be the scan line R1 (located first, for example, from the upper side of the scanning region 1A). Together with already mentioned initialization of the value of the variable counx to 0, the CPU 501 sets the initial scanning point (i.e., the scanning start point) at the scanning point R11.)

At the step of S6, the CPU 501 initializes the value of a variable counxv to be 0.

(The value of the variable counxv is associated with the value of j for a scanning point Rij (i=1 through m, j=1 through n) and specifies the x coordinate of the scanning point Rij (i=1 through m, j=1 through n) measured relative to a scanning region origin 5A.)

(At the step of S6, initializing the value of the variable counxv to be 0, the CPU 501 sets the initial scanning point (i.e., the scanning start point) at a scanning point located, for example, in a left edge on a scan line Ri (i=1 through m).)

At the step of S6, the CPU 501 initializes the value of a variable counyv to be 0.

(The value of the variable counyv is associated with the value of i for a scan line Ri (i=1 through m) and specifies the y coordinate of the scan line Ri (i=1 through m) measured relative to a scanning region origin 5A.)

(At the step of S6, initializing the value of the variable counyv to be 0, the CPU 501 sets the initial scan line (i.e., the starting scan line) to be the scan line R1 located, for example, in an upper side of the scanning region 1A. Together with already mentioned initialization of the value of counxv to 0, the CPU 501 sets the initial scanning point (i.e., the scanning start point) at the scanning point R11.)

At the step of S7, the CPU 501 generates an ID6 window for a visual field mapping screen 3, on an output device (for example, a display 304).

(In an embodiment of the present invention, the CPU 501 sets, for example, the width of 660+150 dots in the x direction and the height of 546−10 dots in the y direction for the visual field mapping screen 3.)

(At the step of S7 in an embodiment of the present invention, the CPU 501 sets the background color of the visual field mapping screen 3 to be the color with R, G, B of the brightness being, for example, 0, 0, 0, respectively, and the visual field mapping screen 3 is set to be colored with the background color by the CPU 501.)

(In an embodiment of the present invention, a visual field mapping screen region corresponding to the scanning region 3A, which is defined by the upper left coordinates, measured relative to a visual field mapping screen origin 6, of (stcounxv, stcounyv) and the lower right coordinates, measured relative to the visual field mapping screen origin 6, of (edx, edy), is set to be colored by a color with R, G, B of brightness being, for example, 20, 0, 25, respectively.)

At the step of S8, the CPU 501 switches the graphic control target to the visual field scanning screen 1.

At the step of S9, the CPU 501 sets a background color of the visual field scanning screen 1.

At the step of S9, the CPU 501 colors the visual field scanning screen 1 with that background color.

(In an embodiment of the present invention, the CPU 501 sets the background color as a color with brightness of R, G, B of, for example, 0, 0, 0, respectively.)

At the step of S10, the CPU 501 sets the display mode (color, size, and shape) of a fixation image 2.

At the step of S10, the CPU 501 displays the fixation image 2 of the above display mode, at the x coordinate, measured relative to the visual field scanning screen origin 5, of, for example, 400 (dots) and the y coordinate, measured relative to the visual field scanning screen origin 5, of, for example, 260 (dots), in the visual field scanning screen 1.

(In an embodiment of the present invention, the CPU 501 sets the color of the fixation image 2 of the display mode to be a color with brightness of R, G, B of, for example, 0, 0, 250, respectively. In an embodiment of the present invention, the CPU 501 represents the fixation image 2, for example, by the symbol of ■, and sets its font size, for example, at 6.)

(For example, a circular form may be used as the shape of the fixation image 2.)

At the step of S11, the CPU 501 sets the display mode (color, size, and shape) of a static visual target.

At the step of S11, the CPU 501 displays the static visual target of the above display mode, at the x coordinate, measured relative to the visual field scanning screen origin 5, of stcounxv+counxv (dots) and the y coordinate, measured relative to the visual field scanning screen origin 5, of stcounyv+counyv (dots), in the visual field scanning screen 1.

At the step of S11, the CPU 501 stores the coordinates in a memory device (for example, such as a RAM 502, a HDD 504, etc.)

(In an embodiment of the present invention, the CPU 501 sets the color of the static visual target of the display mode to be a color with brightness of R, G, B of, for example, 0, 250, 0, respectively. The CPU 501 represents the static visual target, for example, by the symbol of ■, and sets its font size, for example, at 2.)

(The CPU 501 may set the static visual target as a dot.)

(The static visual target may be set in the other size.)

(The step of S11 forms a part of scan line setting means.)

(The step of S11 forms a part of scanning point setting means.)

At the step of S12, the CPU 501 makes a judgement about whether or not the moment of the outset of the response made regarding the visual perception of the static visual target displayed at S11 has been detected via a first input device (for example, a right cursor key 303A in an embodiment of the present invention) or via a second input device (for example, a left cursor key 303B in an embodiment of the present invention).

If the moment of the outset of the response made regarding the visual perception of the static visual target displayed at S11 has not been detected via the first input device (for example, the right cursor key 303A in an embodiment of the present invention) or via the second input device (for example, the left cursor key 303B in an embodiment of the present invention), the CPU 501 goes back to the step of S9 to continue the processing.

(Forming a part of response waiting means.)

In the judgement made by the CPU 501 at the step of S12 about whether or not the moment of the outset of the response made regarding the visual perception of the static visual target displayed at S11 has been detected via the first input device (for example, the right cursor key 303A in an embodiment of the present invention) or via the second input device (for example, the left cursor key 303B in an embodiment of the present invention), if the CPU 501 makes a judgement that the moment of the outset of the response made regarding the visual perception of the static visual target displayed at S11 has been detected via the first input device (for example, the right cursor key 303A in an embodiment of the present invention) or via the second input device (for example, the left cursor key 303B in an embodiment of the present invention), then the CPU 501 moves on to the processing of the step of S13.

At the step of S13, the CPU 501 makes a judgement about whether the detection at S12 was via the first input device (for example, the right cursor key 303A in an embodiment of the present invention).

If the CPU 501 makes a judgement that the detection at S12 was via the first input device (for example, the right cursor key 303A in an embodiment of the present invention), then the CPU 501 moves on to the processing of the step of S19.

In the judgement made by the CPU 501 at the step of S13 about whether the detection at S12 was via the first input device (for example, the right cursor key 303A in an embodiment of the present invention), if the CPU 501 doesn't make the judgement that the detection at S12 was via the first input device (for example, the right cursor key 303A in an embodiment of the present invention), then the CPU 501 moves on to the processing of the step of S14.

At the step of S14, the CPU 501 makes a judgement about whether the detection at S12 was via the second input device (for example, the left cursor key 303B in an embodiment of the present invention).

At the step of S15, the CPU 501 switches the graphic control target to the visual field mapping screen 3.

At the step of S16, the CPU 501 sets the display mode (color, size, and shape) of a visual target perception inability symbol such as f16, f17, f18, f19, f110, f1($n$−1), f1$n$, f21, or f22.

(In an embodiment of the present invention, the CPU 501 sets the color of the visual target perception inability symbol such as f16, f17, f18, f19, f110, f1($n$−1), f1$n$, f21, or f22 to be a color with brightness of R, G, B of, for example, 0, 100, 250, respectively. In an embodiment of the present invention, the CPU 501 represents the visual target perception inability symbol such as f16, f17, f18, f19, f110, f1($n$−1), f1$n$, f21, or f22, for example, by the symbol of ■, and sets its font size, for example, at 2.)

At the step of S17, in reference to the coordinates stored, at S11, in the memory device (for example, such as the RAM 502, the HDD 504, etc.), the CPU 501 displays and records at the position in the visual field mapping screen 3 which corresponds to the coordinates (stored at S11), the visual target perception inability symbol such as f16, f17, f18, f19, f110, f1($n$−1), f1$n$, f21, or f22 representing the inability to visually perceive the static visual target displayed at S11.

That is, at the position of the x coordinate, measured relative to the visual field mapping screen origin 6, of stcounxv+counxv (dots) and the y coordinate, measured relative to the visual field mapping screen origin 6, of stcounyv+counyv (dots) in the visual field mapping screen 3, displaying and recording the symbol which represents the inability to visually perceive the static visual target at the corresponding position of the visual field scanning screen 1.

At the step of S18, the CPU 501 switches the graphic control target to the visual field scanning screen 1.

At the step of S19, the CPU 501, by carrying out the computation using an arithmetic unit, increments the value of the variable counx by one and stores the result on the memory device (for example, such as the RAM 502, the HDD 504, etc.).

The CPU 501 reads out the value of the above result from the memory device (for example, such as the RAM 502, the HDD 504, etc.), carries out through the arithmetic unit the computation of its multiplication by, for example, 5, and substitutes the obtained value into the variable counxv, which is stored on the memory device (for example, such as the RAM 502, the HDD 504, etc.).

(In an embodiment of the present invention, the variable counx is for the CPU 501 to cause a move of a scanning point Rij (i=1 through m, j=1 through n) along a scan line Ri (i=1 through m).)

(The value of the variable counx is associated with the value of j for a scanning point Rij (i=1 through m, j=1 through n). In an embodiment of the present invention, the value of counx+1 specifies the value of j.)

(The 5, by which the variable counx is multiplied, set the scanning point interval at, for example, 5, along the scan line Ri (i=1 through m). A scanning point interval may be set otherwise.)

(The value of the variable counxv is associated with the value of j for a scanning point Rij (i=1 through m, j=1 through n) and specifies the x coordinate of the scanning point Rij (i=1 through m, j=1 through n) measured relative to the scanning region origin 5A.)

(The step of S19 forms a part of scan line setting means.)
(The step of S19 forms a part of scanning point setting means.)

At the step of S20, the CPU 501 reads out the value of the variable stcounxv stored in the memory device (for example, such as the RAM 502, the HDD 504, etc.).

At the step of S20, the CPU 501 reads out the value of the variable counxv calculated and stored, at the step of S19, in the memory device (for example, such as the RAM 502, the HDD 504, etc.).

At the step of S20, the CPU 501, using the arithmetic unit, carries out the addition of stcounxv, which is a value read out from the memory device (for example, such as the RAM 502, the HDD 504, etc.), and counxv, which is a value read out from the memory device (for example, such as the RAM 502, the HDD 504, etc.), and the result obtained is substituted into the variable stcounxvz to store in the memory device (for example, such as the RAM 502, the HDD 504, etc.) by the CPU 501.

At the step of S21, the CPU 501, using the arithmetic unit, makes a judgement about whether stcounxvz>edx, based on the read out value of the variable stcounxvz calculated and stored in the memory device (for example, such as the RAM 502, the HDD 504, etc.) at the step of S20, and the read out value of variable edx stored in the memory device (for example, such as the RAM 502, the HDD 504, etc.)

If the CPU 501, using the arithmetic unit, makes a judgement that stcounxvz>edx does not hold, then the CPU 501 goes back to the step of S9 to continue the processing.

At the step of S21, if the CPU 501, using the arithmetic unit, makes a judgement that stcounxvz>edx holds, then the CPU 501 moves on to the processing of the step of S22.

At the step of S22, the CPU 501, by carrying out the computation using the arithmetic unit, increments the value of the variable couny by one and stores the result on the memory device (for example, such as the RAM 502, the HDD 504, etc.).

The CPU 501 reads out the value of the above result from the memory device (for example, such as the RAM 502, the HDD 504, etc.), carries out through the arithmetic unit the computation of its multiplication by, for example, 5, and substitutes the obtained value into the variable counyv, which is stored on the memory device (for example, such as the RAM 502, the HDD 504, etc.).

(In an embodiment of the present invention, the variable couny is for the CPU 501, when having completed the scan of a scan line, to switch the scan line Ri (i=1 through m) to its adjacent scan line Ri (i=1 through m))

(The value of the variable couny is associated with the value of i for a scan line Ri (i=1 through m). In an embodiment of the present invention, the value of couny+1 specifies the value of i.)

(The 5, by which the variable couny is multiplied, set the scan line interval of the scan line Ri (i=1 through m) at, for example, 5, in the visual field scanning screen 1. A scan line interval may be set otherwise.)

(The value of the variable counyv is associated with the value of i for a scan line Ri (i=1 through m) and specifies the y coordinate of the scan line Ri (i=1 through m) measured relative to the scanning region origin 5A.)

(The step of S22 forms a part of scan line setting means.)
(The step of S22 forms a part of scanning point setting means.)

At the step of S23, the CPU 501 initializes the value of the variable counx to be 0, which is stored in the memory device (for example, such as the RAM 502, the HDD 504, etc.).

At the step of S23, the CPU 501 reads out the initialized value of the counx from the memory device (for example, such as the RAM 502, the HDD 504, etc.), carries out through the arithmetic unit the computation of its multiplication by, for example, 5, and substitutes the obtained value into the variable counxv, which is stored on the memory device (for example, such as the RAM 502, the HDD 504, etc.).

(The initialization of the variable counx to 0 by the CPU 501 at the step of S23 is for the setting of initializing the scanning point, at the time of switching the scan line, to the first scanning point, for example, from the left on the scan line Ri (i=1 through m). Setting the scan line Ri (i=1 through m) in the scanning region 1A.)

(The initialization of the variable counxv to 0 by the CPU 501 using the arithmetic unit, followed by the initialization of the variable counx to 0 by the CPU 501, is for the setting of initializing the scanning point, at the time of switching the scan line, to the scanning point located, for example, in a left edge of the scan line Ri (i=1 through m). Setting the scan line Ri (i=1 through m) in the scanning region 1A.)

(The step of S23 forms a part of scan line setting means.)
(The step of S23 forms a part of scanning point setting means.)

At the step of S24, the CPU 501 reads out the value of the variable stcounyv stored in the memory device (for example, such as the RAM 502, the HDD 504, etc.).

At the step of S24, the CPU 501 reads out the value of the variable counyv calculated and stored, at the step of S22, in the memory device (for example, such as the RAM 502, the HDD 504, etc.).

At the step of S24, the CPU 501, using the arithmetic unit, carries out the addition of stcounyv, which is a value read out from the memory device (for example, such as the RAM 502, the HDD 504, etc.), and counyv, which is a value read out from the memory device (for example, such as the RAM 502, the HDD 504, etc.), and the result obtained is substituted into the variable stcounyvz to store in the memory device (for example, such as the RAM 502, the HDD 504, etc.) by the CPU 501.

At the step of S25, the CPU 501, using the arithmetic unit, makes a judgement about whether stcounyvz>edy, based on the read out value of the variable stcounyvz calculated and stored in the memory device (for example, such as the RAM 502, the HDD 504, etc.) at the step of S24, and the read out value of variable edy stored in the memory device (for example, such as the RAM 502, the HDD 504, etc.)

If the CPU 501, using the arithmetic unit, makes a judgement that stcounyvz>edy does not hold, then the CPU 501 goes back to the step of S9 to continue the processing.

At the step of S25, if the CPU 501, using the arithmetic unit, makes a judgement that stcounyvz>edy holds, then the CPU 501 moves on to the processing of the step of S26.

At the step of S26, the CPU 501 switches the graphic control target to the visual field mapping screen 3.

At the step of S27, the display mode (color, size, and shape) of a fixation image in the visual field mapping screen 4 to be recorded in the visual field mapping screen 3 is set by the CPU 501.

(In an embodiment of the present invention, the CPU 501 sets the color of the fixation image in the visual field mapping screen 4 of the display mode to be a color with brightness of R, G, B of, for example, 100, 250, 200, respectively. The CPU 501 represents the fixation image in the visual field mapping screen 4, for example, by the symbol of ■, and sets its font size, for example, at 6.)

At the step of S28, the fixation image in the visual field mapping screen 4 of the display mode set at the step of S27 is displayed and recorded at the position in the visual field mapping screen 3 which corresponds to the display position of the fixation image 2 in the visual field scanning screen 1, i.e., in an embodiment of the present invention displayed and recorded at the position of the x coordinate, measured relative to the visual field mapping screen origin 6, of 400 (dots) and the y coordinate, measured relative to the visual field mapping screen origin 6, of 260 (dots).

What is claimed is:

1. An operational method for a static visual field scanning apparatus comprising:

A step of means for generating, on an output device, a visual field scanning screen for scanning a visual field of a subject using a static visual target;

A step of means for setting an area to be scanned by the static visual target, as a scanning region, on the visual field scanning screen that is generated, on the output device, by said step of visual field scanning screen generating means;

A step of means for displaying and controlling a fixation image to be fixated by the subject, during a visual field scanning, on the visual field scanning screen generated by said step of visual field scanning screen generating means;

A step of means for setting at least one scan line on said visual field scanning screen;

A step of means for setting at least one scanning point along the scan line set by said step of scan line setting means;

A step of means for displaying and controlling the static visual target at a scanning point among the scanning points, to scan the visual field corresponding to said scanning point, which are set, along the scan line, by said step of scanning point setting means;

A step of means for detecting the response to be made, via a first input device, at the time when the static visual target, displayed by said step of visual target displaying and controlling means, is perceived;

A step of means for detecting the response to be made, via a second input device, at the time when the static visual target, displayed by said step of visual target displaying and controlling means, cannot be perceived;

A step of means for generating a visual field mapping screen, on an output device, to map and display the subject's visual field;

A step of means, through said step of visual target displaying and controlling means, for continuing the scan of the visual field corresponding to a next scanning point by displaying the static visual target to scan the visual field corresponding to the next scanning point, at the next scanning point among the scanning points set by said step of scanning point setting means, immediately after stopping displaying, promptly when detecting the response via said first input device through said step of the first detection means, the static visual target displayed by said step of visual target displaying and controlling means at the time of said detection;

A step of means, through said step of visual target displaying and controlling means, for continuing the scan of the visual field corresponding to a next scanning point by displaying the static visual target to scan the visual field corresponding to the next scanning point, at the next scanning point among the scanning points set by said step of scanning point setting means, immediately after stopping displaying, promptly when detecting the response via said second input device through said step of the second detection means, the static visual target displayed by said step of visual target displaying and controlling means at the time of said detection;

A step of means for storing in a memory device the coordinates of the static visual target displayed, either at the time of the response via said first input device being detected through said step of the first detection means or at the time of the response via said second input device being detected through said step of the second detection means, by said step of visual target displaying and controlling means;

A step of means for, when the response via said second input device is detected by said step of the second detection means, recording, in reference to the coordinates stored in the memory device at the time of said detection by said step of visual target display coordinates storing means, at a position of said visual field mapping screen which corresponds to said coordinates, a symbol which represents the inability to visually perceive the static visual target displayed at said coordinates by said step of visual target displaying and controlling means;

A step of means, through said step of continuing the scan of the visual field corresponding to a next scanning point immediately after detection by the first input device means, for, when the response via said first input device is detected by said step of the first detection means, making a judgement, using an arithmetic unit, about whether the scan of the scanning points along a scan line which the static visual target displayed by said step of visual target displaying and controlling means at the time of said detection, belonged to and lay at has been completed or not;

A step of means, through said step of continuing the scan of the visual field corresponding to a next scanning point immediately after detection by the second input device means, for, when the response via said second input device is detected by said step of the second detection means, making a judgement, using the arithmetic unit, about whether the scan of the scanning points along a scan line which the static visual target displayed by said step of visual target displaying and controlling means at the time of said detection, belonged to and lay at has been completed or not;

A step of means, through said step of continuing the scan of the visual field corresponding to a next scanning point immediately after detection by the first input device means, for, when the scan of the scanning points on a scan line is judged to be uncompleted by said step of the first completion judgement means, designating through the calculation of the arithmetic unit as the next scanning point the scanning point that shares the scan line with, and is adjacent to, the static visual target displayed at the time of the response via said first input device being detected through said step of the first detection means, by said step of visual target displaying and controlling means, and for, when the scan of the scanning points on a scan line is judged to be completed by said step of the first completion judgement means, through the calculation of the arithmetic unit, switching the scan line for scanning to the scan line adjacent to the scan line which the static visual target displayed by said step of visual target displaying and controlling means at the time of the response, via said first input device, being detected through said step of the first detection means, belonged to and lay at, and designating as the next scanning point the scanning point that lies in an edge of said scan line;

And a step of means, through said step of continuing the scan of the visual field corresponding to a next scanning point immediately after detection by the second input device means, for, when the scan of the scanning points on a scan line is judged to be uncompleted by said step of the second completion judgement means, designating through the calculation of the arithmetic unit as the next scanning point the scanning point that shares the scan line with, and is adjacent to, the static visual target displayed at the time of the response via said second input device being detected through said step of the second detection means, by said step of visual target displaying and controlling means, and for, when the scan of the scanning points on a scan line is judged to be completed by said step of the second completion judgement means, through the calculation of the arithmetic unit, switching the scan line for scanning to the scan line adjacent to the scan line which the static visual target displayed by said step of visual target displaying and controlling means at the time of the response, via said second input device, being detected through said step of the second detection means, belonged to and lay at, and designating as the next scanning point the scanning point that lies in an edge of said scan line.

2. A non-transitory computer-readable recorded medium recording a program for causing a computer to realize the function comprising:

Means for generating, on an output device, a visual field scanning screen for scanning a visual field of a subject using a static visual target;

Means for setting an area to be scanned by the static visual target, as a scanning region, on the visual field scanning screen that is generated, on the output device, by said visual field scanning screen generating means;

Means for displaying and controlling a fixation image to be fixated by the subject, during a visual field scanning, on the visual field scanning screen generated by said visual field scanning screen generating means;

Means for setting at least one scan line on said visual field scanning screen;

Means for setting at least one scanning point along the scan line set by said scan line setting means;

Means for displaying and controlling the static visual target at a scanning point among the scanning points, to scan the visual field corresponding to said scanning point, which are set, along the scan line, by said scanning point setting means;

Means for detecting the response to be made, via a first input device, at the time when the static visual target, displayed by said visual target displaying and controlling means, is perceived;

Means for detecting the response to be made, via a second input device, at the time when the static visual target, displayed by said visual target displaying and controlling means, cannot be perceived;

Means for generating a visual field mapping screen, on an output device, to map and display the subject's visual field;

Means, through said visual target displaying and controlling means, for continuing the scan of the visual field corresponding to a next scanning point by displaying the static visual target to scan the visual field corresponding to the next scanning point, at the next scanning point among the scanning points set by said scanning point setting means, immediately after stopping displaying, promptly when detecting the response via said first input device through said first detection means, the static visual target displayed by said visual target displaying and controlling means at the time of said detection;

Means, through said visual target displaying and controlling means, for continuing the scan of the visual field corresponding to a next scanning point by displaying the static visual target to scan the visual field corresponding to the next scanning point, at the next scanning point among the scanning points set by said scanning point setting means, immediately after stopping displaying, promptly when detecting the response via said second input device through said second detection means, the static visual target displayed by said visual target displaying and controlling means at the time of said detection;

Means for storing in a memory device the coordinates of the static visual target displayed, either at the time of the response via said first input device being detected through said first detection means or at the time of the response via said second input device being detected through said second detection means, by said visual target displaying and controlling means;

Means for, when the response via said second input device is detected by said second detection means, recording, in reference to the coordinates stored in the memory device at the time of said detection by said visual target display coordinates storing means, at a position of said visual field mapping screen which corresponds to said coordinates, a symbol which represents the inability to visually perceive the static visual target displayed at said coordinates by said visual target displaying and controlling means;

Means, through said continuing the scan of the visual field corresponding to a next scanning point immediately after detection by the first input device means, for, when the response via said first input device is detected by said first detection means, making a judgement, using an arithmetic unit, about whether the scan of the scanning points along a scan line which the static visual target displayed by said visual target displaying and controlling means at the time of said detection, belonged to and lay at has been completed or not;

Means, through said continuing the scan of the visual field corresponding to a next scanning point immediately after detection by the second input device means, for, when the response via said second input device is detected by said second detection means, making a judgement, using the arithmetic unit, about whether the scan of the scanning points along a scan line which the static visual target displayed by said visual target displaying and controlling means at the time of said detection, belonged to and lay at has been completed or not;

Means, through said continuing the scan of the visual field corresponding to a next scanning point immediately after detection by the first input device means, for, when the scan of the scanning points on a scan line is judged to be uncompleted by said first completion judgement means, designating through the calculation of the arithmetic unit as the next scanning point the scanning point that shares the scan line with, and is adjacent to, the static visual target displayed at the time of the response via said first input device being detected through said first detection means, by said visual target displaying and controlling means, and for, when the scan of the scanning points on a scan line is judged to be completed by said first completion judgement means, through the calculation of the arithmetic unit, switching the scan line for scanning to the scan line adjacent to the scan line which the static visual target displayed by said visual target displaying and controlling means at the time of the response, via said first input device, being detected through said first detection means, belonged to and lay at, and designating as the next scanning point the scanning point that lies in an edge of said scan line;

And means, through said continuing the scan of the visual field corresponding to a next scanning point immediately after detection by the second input device means, for, when the scan of the scanning points on a scan line is judged to be uncompleted by said second completion judgement means, designating through the calculation of the arithmetic unit as the next scanning point the scanning point that shares the scan line with, and is adjacent to, the static visual target displayed at the time of the response via said second input device being detected through said second detection means, by said visual target displaying and controlling means, and for, when the scan of the scanning points on a scan line is judged to be completed by said second completion judgement means, through the calculation of the arithmetic unit, switching the scan line for scanning to the scan line adjacent to the scan line which the static visual target displayed by said visual target displaying and controlling means at the time of the response, via said second input device, being detected through said second detection means, belonged to and lay at, and designating as the next scanning point the scanning point that lies in an edge of said scan line.

* * * * *